(12) United States Patent
Mizrahi et al.

(10) Patent No.: US 11,951,138 B2
(45) Date of Patent: Apr. 9, 2024

(54) MICROBIAL COMPOSITIONS COMPRISING RUMEN MICROFLORA AND USES THEREOF

(71) Applicant: The State of Israel, Ministry of Agriculture & Rural Development, Agricultural Research Organization (ARO) (Volcani Center), Beit-Dagan (IL)

(72) Inventors: Itzhak Mizrahi, Tel-Aviv (IL); Elie Jami, Bat-Yam (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 0 days.

(21) Appl. No.: 14/773,887

(22) PCT Filed: Mar. 13, 2014

(86) PCT No.: PCT/IL2014/050277
§ 371 (c)(1),
(2) Date: Sep. 9, 2015

(87) PCT Pub. No.: WO2014/141274
PCT Pub. Date: Sep. 18, 2014

(65) Prior Publication Data
US 2016/0015757 A1 Jan. 21, 2016

Related U.S. Application Data

(60) Provisional application No. 61/782,783, filed on Mar. 14, 2013.

(51) Int. Cl.
| | |
|---|---|
| A61K 35/74 | (2015.01) |
| A23K 10/18 | (2016.01) |
| A23K 20/195 | (2016.01) |
| A23K 50/10 | (2016.01) |
| A23K 50/60 | (2016.01) |
| A61K 35/66 | (2015.01) |
| C12N 1/20 | (2006.01) |
| C12Q 1/6869 | (2018.01) |
| C12Q 1/689 | (2018.01) |

(52) U.S. Cl.
CPC .............. *A61K 35/74* (2013.01); *A23K 10/18* (2016.05); *A23K 20/195* (2016.05); *A23K 50/10* (2016.05); *A23K 50/60* (2016.05); *A61K 35/66* (2013.01); *C12N 1/20* (2013.01); *C12Q 1/6869* (2013.01); *C12Q 1/689* (2013.01); *C12Q 2600/124* (2013.01)

(58) Field of Classification Search
CPC ...... A61K 35/74; A61K 35/66; A61K 35/741; C12N 1/20; C12N 1/205; A23K 10/18; A23K 50/10
See application file for complete search history.

(56) References Cited

U.S. PATENT DOCUMENTS

| | | | |
|---|---|---|---|
| 4,138,498 A | 2/1979 | Das | |
| 7,291,328 B2 | 11/2007 | Garner et al. | |
| 8,771,723 B2 | 7/2014 | Perdok et al. | |
| 2014/0099406 A1 | 4/2014 | Hoffmann Pegoraro et al. | |
| 2014/0199281 A1* | 7/2014 | Henn ..................... | A61K 38/13 424/93.46 |
| 2020/0123588 A1 | 4/2020 | Mizrahi | |
| 2021/0164013 A1 | 6/2021 | Mizrahi | |

FOREIGN PATENT DOCUMENTS

| | | |
|---|---|---|
| EP | 0299183 | 1/1989 |
| WO | WO 2011/010921 | 1/2011 |
| WO | WO 2012/110777 | 8/2012 |
| WO | WO 2014/141274 | 9/2014 |
| WO | WO 2016/03343 | 1/2016 |
| WO | WO 2016/033439 | 3/2016 |
| WO | WO 2017/120495 | 7/2017 |
| WO | WO 2017/187433 | 11/2017 |

OTHER PUBLICATIONS

Seo et al., Direct-Fed Microbials for Ruminant Animals, Asian-Aust. J. Anim. Sci. 23 (12): 1657-1667.*
Kong et al., Composition, spatial distribution, and diversity of the bacterial communities in the rumen of cows fed different forages, FEMS Microbiol Ecol 74 (2010) 612-622.*
Krehbiel et al., Bacterial direct-fed microbials in ruminant diets: Performance response and mode of action, J. ANim. Sci. 81 (E. Suppl. 2): E120-E132 2003.*
Singh et al., Metagenomics in animal gastrointestinal ecosystem: a microbiological and biotechnological perspective, Indain J. Microbiol. (Jun. 2008) 48: 216-227.*
Koike et al., Asian-Aust. J. Anim. Sci., 2009, 22(1): 131-138. (Year: 2009).*
Van Gylswyk, FEMS Microbiology Ecology, 1990, 73: 243-254. (Year: 1990).*
Mao et al., Anaerobe, 24:12-19, 2013. (Year: 2013).*
Satter et al., Dairy Science, 1969, 52 (11): 1776-1780 (Year: 1969).*

(Continued)

*Primary Examiner* — Allison M Fox
*Assistant Examiner* — Qing Xu

(57) ABSTRACT

A method of mimicking a phenotype of a first ruminating animal in a second ruminating animal is disclosed. The method comprises administering to the second ruminating animal a microbial composition comprising a plurality of microbes having a signature which is statistically significantly similar to the microbial signature of a rumen microbiome of the first ruminating animal, wherein the first and the second ruminating animal are of identical species, thereby mimicking the phenotype of the first ruminating animal in the second ruminating animal.

11 Claims, 7 Drawing Sheets
(6 of 7 Drawing Sheet(s) Filed in Color)
Specification includes a Sequence Listing.

(56) References Cited

OTHER PUBLICATIONS

Frizzo et al., Animal Feed Science and Technology, 2010, 157:159-167 (Year: 2010).*
International Search Report and the Written Opinion dated Feb. 26, 2017 From the International Searching Authority Re. Application No. PCT/IL2016/051197. (15 Pages).
Invitation to Pay Additional Fees and Communication Relating to the Results of the Partial International Search dated Jan. 23, 2017 From the International Searching Authority Re. Application No. PCT/IL2016/051197. (5 Pages).
Carberry et al. "Effect of Phenotype Residual Feed Intake and Dietary Forage Content on the Rumen Microbial Community of Beef Cattle", Applied and Environmental Microbiology, 78(14): 4949-4958, Published Online May 4, 2012.
Carberry et al. "Rumen Methanogenic Genotypes Differ in Abundance According to Host Residual Feed Intake Phenotype and Diet Type", Applied and Environmental Microbiology, 80(2): 586-594, Published Online Nov. 8, 2013.
Kittelmann et al. "Two Different Bacterial Community Types are Linked With the Low-Methane Emission Trait in Sheep", PLoS ONE, 9(7): e103171-1-e103171-9, Published Online Jul. 31, 2014.
Shabat et al. "Specific Microbiome-Dependent Mechanisms Underlie the Energy Harvest Efficiency of Ruminants", The ISME Journal, 10(12): 2958-2972, Published Online May 6, 2016.
Zhou et al. "Assessment of the Microbial Ecology of Ruminal Methanogens in Cattle With Different Feed Efficiencies", Applied and Environmental Microbiology, 75(20): 6524-6533, Published Ahead of Print Aug. 28, 2009. Abstract, P.6526, Left col. Table 3.
International Preliminary Report on Patentability dated Sep. 24, 2015 From the International Bureau of WIPO Re. Application No. PCT/IL2014/050277.
International Search Report and the Written Opinion dated Jun. 15, 2014 From the International Searching Authority Re. Application No. PCT/IL2014/050277.
Chiquette et al. "Prevotella Bryantii 25A Used as a Probiotic in Early-Lactation Dairy Cows: Effect on Ruminal Fermentation Characteristics, Milk Production, and Milk Composition", Journal of Dairy Science, 91: 3536-3543, 2008.
Guan et al. "Linkage of Microbial Ecology to Phenotype: Correlation of Rumen Microbial Ecology to Cattle's Feed Efficiency", FEMS Microbiology Letters, 288(1): 85-91, Nov. 2008. P.89, Left col. Last Para—P.90, Right col. 1st Para.
Hernandez-Sanabria et al. "Correlation of Particular Bacterial PCR-Denaturing Gradient Gel Electrophoresis Patterns With Bovine Ruminal Fermentation Parameters and Feed Efficiency Traits", Applied and Environmental Microbiology, 76(19): 6338-6350, Oct. 2010.
Jami et al. "Composition and Similarity of Bovine Rumen Microbiota Across Individual Animals", PLoS ONE, 7(3): e33306-1-e33306-8, Mar. 2012. Figs.2, 4.
Jami et al. "Potential Role of the Bovine Rumen Microbiome in Modulating Milk Composition and Feed Efficiency", PLoS ONE, 9(1): e85423-1-e85423-6, Jan. 22, 2014.
Jami et al. "Similarity of the Ruminal Bacteria Across Individual Lactating Cows", Anaerobe, 18(3): 338-342, Apr. 21, 2012.
Krause et al. "Opportunities to Improve Fiber Degradation in the Rumen: Microbiology, Ecology, and Genomics", FEMS Microbiology Reviews, 27: 663-693, 2003.
Li et al. "Effect of Sampling Location and Time, and Host Animal on Assessment of Bacterial Diversity and Fermentation Parameters in the Bovine Rumen", Journal of Applied Microbiology, 107: 1924-1934, 2009.
Weimer et al. "Host Specificity of the Ruminal Bacterial Community in the Dairy Cow Following Near-Total Exchange of Ruminal Contents", Journal of Dairy Science, 93(12): 5902-5912, Dec. 2010. Abstract, Figs.5, 6, Discussion Section.

West et al. "Effects of Addition of Bacterial Inoculants to the Diets of Lactating Diary Cows on Feed Intake, Milk Yield, and Milk Composition", The Professional Animal Scientist, 27: 122-126, 2011.
International Preliminary Report on Patentability dated Nov. 8, 2018 From the International Bureau of WIPO Re. Application No. PCT/IL2016/051197. (9 Pages).
Examination Report dated Dec. 17, 2019 From the Servico Publico Federal, Ministerio da Economia, Instututo Nacional da Propriedade Industrial do Brasil Re. Application No. BR112018072105-0. (4 Pages).
Translation dated Jan. 23, 2020 of Examination Report dated Dec. 17, 2019 From the Servico Publico Federal, Ministerio da Economia, Instututo Nacional da Propriedade Industrial do Brasil Re. Application No. BR112018072105-0. (5 Pages).
Notification of Necessity to Provide Additional Materials dated Feb. 21, 2020 From the Eurasian Patent Organization, Eurasian Patent Office Re. Application No. 201892404 and Its Translation Into English. (7 Pages).
Restriction Official Action dated Mar. 2, 2020 From the US Patent and Trademark Office Re. U.S. Appl. No. 16/096,349. (6 pages).
Examination Report dated Mar. 25, 2021 From the Australian Government, IP Australia Re. Application No. 2016404864. (3 Pages).
Notification of Necessity to Provide Additional Materials dated Nov. 26, 2020 From the Eurasian Patent Organization, Eurasian Patent Office Re. Application No. 201892404 and Its Translation Into English. (3 Pages).
Official Action dated Jun. 19, 2020 from the US Patent and Trademark Office Re. U.S. Appl. No. 16/096,349. (18 pages).
Examination Report dated Jun. 25, 2021 From the Instituto Mexicano de la Propiedad Industrial, Direccion Divisional de Patentes Re. Application No. MX/a/2018/013050 and Its Translation Into English. (9 Pages).
Patent Examination Report dated Sep. 7, 2021 From the Australian Government, IP Australia Re. Application No. 2016404864. (10 Pages).
Patra et al. "Effects of Vanillin, Quillaja Saponin, and Essential Oils on In Vitro Fermentation and Protein-Degrading Microorganisms of the Rumen", Applied Microbiology and Biotechnology, 98:897-905, Published Online Apr. 30, 2013.
Weimer et al. "Fiber Digestion, VFA Production, and Microbial Population Changes During In Vitro Ruminal Fermentations of Mixed Rations by Monensin-Adapted and Unadapted Microbes", Animal Feed Science and Technology, 169(1-2:68-78, Oct. 13, 2011.
Examination Report dated Nov. 6, 2020 From the Australian Government, IP Australia Re. Application No. 2016404864. (6 Pages).
Examination Report dated Oct. 28, 2021 From the Instituto Mexicano de la Propiedad Industrial, Direccion Divisional de Patentes Re. Application No. MX/a/2018/013050 and Its Translation Into English. (11 Pages).
Technical Examination Report dated Dec. 2, 2021 From the Servico Publico Federal, Ministerio da Economia, Instituto Nacional da Propriedade Industrial do Brasil Re. Application No. BR112018072105-0 and Its Translation Into English. (12 Pages).
Examination Report dated Jul. 4, 2022 From the Servico Publico Federal, Ministerio da Economia, Instituto Nacional da Propriedade Industrial do Brasil RE Application No. BR112013014918.3 and Its English Summary . . . (8 Pages).
Examination Report dated Jul. 4, 2022 From the Servico Publico Federal, Ministerio da Economia, Instituto Nacional da Propriedade Industrial do Brasil RE Application No. BR12 2022 006020 0 and Its English Summary. (6 Pages).
Examination Report dated Jul. 4, 2022 From the Servico Publico Federal, Ministerio da Economia, Instituto Nacional da Propriedade Industrial do Brasil RE Application No. BR112013014918.3 and its English Summary.(7 Pages).
Examination Report dated Jul. 4, 2022 From the Servico Publico Federal, Ministerio da Economia, Instituto Nacional da Propriedade Industrial do Brasil RE Application No. BR12 2022 006011 0 and Its English Summary. (10 Pages).

(56) References Cited

OTHER PUBLICATIONS

Examination Report dated Jul. 4, 2022 From the Servico Publico Federal, Ministerio da Economia, Instituto Nacional da Propriedade Industrial do Brasil RE Application No. BR12 2022 006026 9 and Its English Summary . . . (8 Pages).
Examination Report dated Jul. 4, 2022 From the Servico Publico Federal, Ministerio da Economia, Instituto Nacional da Propriedade Industrial do Brasil RE Application No. BR12 2022 006027 7 and Its English Summary. (8 Pages).
Notification About Necessity to Submit Additional Materials dated Jul. 22, 2022 From The Eurasian Patent Organization, The Eurasian Patent Office Re. Application No. 202290067 andits Translation into English. (4 Pages).
Bertram et al. "A Metabolomic Investigation of Splanchnic Metabolism Using 1H NMR Spectroscopy of Bovine Blood Plasma", Analytica Chimica Acta, 536(1-2): 1-6, Apr. 22, 2005.
Flint et al. "Links Between Diet, Gut Microbiota Composition and Gut Metabolism", Proceedings of the Nutrition Society, 74(1): 13-22, Sep. 30, 2014.
Kobayashi et al. "Abatement of Methane Production from Ruminants: Trends in the Manipulation of Rumen Fermentation", Asian-Australasian Journal of Animal Sciences, 23(3): 410-416, Mar. 1, 2010.
Saleem et al. "The Bovine Ruminal Fluid Metabolome", Metabolomics, 9(2): 360-378, Sep. 11, 2012.
Examination Report dated Jul. 4, 2022 From the Servico Publico Federal, Ministerio da Economia, Instituto Nacional da Propriedade Industrial do Brasil RE Application No. BR11 2018 072105-0 and Its English Summary. (10 Pages).
Examination Report dated Jan. 18, 2023 From the Australian Government, IP Australia Re. Application No. 2022200755. (5 Pages).
Technical Examination Report dated Feb. 2, 2023 From the Servico Publico Federal, Ministerio da Economia, Instituto Nacional da Propriedade Industrial do Brasil Re. Application No. BR122022006026 9 and English Summary. (7 Pages).
Technical Examination Report dated Feb. 2, 2023 from the National Institute of Industrial Property of Brazil Re. Application No. BR 12 2022 006027 7 with an English Summary. (5 pages).
Translation dated Apr. 3, 2023 of Technical Examination Report dated Feb. 2, 2023 from the National Institute of Industrial Property of Brazil Re. Application No. BR 12 2022 006027 7. (4 pages).
Requisition by the Examiner dated Sep. 23, 2022 From the Innovation, Science and Economic Development Canada, Canadian Intellectual Property Office Re. Application No. 3,022,023. (6 pages).
Technical Examination Report dated Aug. 1, 2022 from the National Institute of Industrial Property of Brazil Re. Application No. BR12 2022 006011 0 and English Summary. (7 Pages).
Relatório de Busca e Parecer [Search Report and Opinion] dated Apr. 6, 2023 From the Serviço Público Federal, Ministério da Economia, Instituto Nacional da Propriedade Industrial do Brasil Re. Application No. BR 12 2022 006027 7. (5 Pages).
Restriction Official Action dated Apr. 28, 2023 From the US Patent and Trademark Office Re. U.S. Appl. No. 17/170,937. (8 Pages).

\* cited by examiner

MICROBIAL COMPOSITIONS COMPRISING RUMEN MICROFLORA AND USES THEREOF

RELATED APPLICATIONS

This application is a National Phase of PCT Patent Application No. PCT/IL2014/050277 having International filing date of Mar. 13, 2014, which claims the benefit of priority under 35 USC §119(e) of U.S. Provisional Patent Application No. 61/782,783 filed on Mar. 14, 2013. The contents of the above applications are all incorporated by reference as if fully set forth herein in their entirety.

SEQUENCE LISTING STATEMENT

The ASCII file, entitled 64029SequenceListing. txt, created on Sep. 7, 2015, comprising 1,067 bytes, submitted concurrently with the filing of this application is incorporated herein by reference.

FIELD AND BACKGROUND OF THE INVENTION

The present invention, in some embodiments thereof, relates to rumen microflora and uses thereof. In one embodiment, the present invention relates to rumen microflora in order to regulate milk production in ruminating animals.

The bovine rumen houses a complex microbiota responsible for cattle ability to convert indigestible plant mass into energy. This ability is of tremendous importance to mankind, with domesticated animals being a crucial intermediate of photosynthesis for production of digestible products such as milk and meat. The rumen functions as a pre-gastric anaerobic fermentation chamber inhabited by a high density microbial community composed of microorganisms from all domains of life. The main component of this microbial community is bacteria, accounting for 95% of the microbial community in the rumen.

Recently, many attempts at improving production yield through modulation of the bacterial community have been attempted. These studies focused mainly on increasing the abundance of known cellulose degrading bacteria, during early stages of animal development, to accomplish this feat (Krause et al., 2003, EMS Microbiol Rev 27:663-93). However, aside from temporary increase of the inoculums, no long-term bacterial fixation or improvement of product yield could be achieved. Moreover, no clear association between the production abilities of cattle and specific microbial taxa was ever demonstrated.

Recent studies, using DGGE community fingerprinting method suggested such an association, by showing differential production of specific volatile fatty acids (VFA) between cows identified as being efficient against inefficient cows (Hernandez-Sanabria et al, 2010, Appl Environ Microbiol 76:6338-50). Different bacteria produce different VFA, inferring the possible link between the animals' efficiency and its resident microbiota. Li et al., (2009 Appl Microbiol 107:1924-34) showed that within the same cow the microbial community remains stable throughout different time points. In other hosts species, such as the mouse or human, a connection between the microbiota and the energy harvest abilities of the animals have been demonstrated when genetically predisposed obese mice exhibited a different Firmicutes/Bacteroidetes ratio (Turnbaugh et al., 2006, Nature 444:1027-31). The transfer of microbiota from obese mice to lean mice resulted in significant physiological changes in the mice, related to adiposity in tissue, suggesting a causative effect of the microbiota on the its host physiology. They concluded that the "obese" microbiome has an increased capacity to harvest energy from the diet.

U.S. Pat. No. 7,291,328 teaches administering an amount of a lactic acid producing bacterium such as *Lactobacillus acidophilus* alone or in combination with a lactate utilizing bacterium such as *Propionibacterium freudenreichii* effective to to enhance the milk fat content of a dairy cow.

European Patent No. EP0299183 A2 teaches a method of increasing the protein content of milk in milk-producing animals by introducing into the animal a culture of one or more non-pathogenic lactic acid producing bacteria.

West et al., [The Professional Animal Scientist 2 7 (2011): 122-126] teach supplemental bacterial inoculants containing *P. freudenreichii* and *L. acidophilus* can improve milk yield and apparent efficiency of nutrient utilization.

Additional background art includes Jamie et al., Jan. 22 2014, Plos1 "Potential Role of the Bovine Rumen Microbiome in Modulating Milk Composition and Feed Efficiency".

SUMMARY OF THE INVENTION

According to an aspect of some embodiments of the present invention there is provided a method of mimicking a phenotype of a first ruminating animal in a second ruminating animal comprising administering to the second ruminating animal a microbial composition comprising a plurality of microbes having a signature which is statistically significantly similar to the microbial signature of a rumen microbiome of the first ruminating animal, wherein the first and the second ruminating animal are of identical species, thereby mimicking the phenotype of the first ruminating animal in the second ruminating animal.

According to an aspect of some embodiments of the present invention there is provided an isolated microbial composition comprising statistically significantly similar microbes to the microbiome of the rumen of a ruminating animal.

According to an aspect of some embodiments of the present invention there is provided a microbial composition comprising a plurality of microbes, the composition having a Firmicutes-to-Bacteroidetes ratio above 1.6, a percent of *Eubacterium* greater than 0.6% and a percent of Lachnospiraceae greater than about 8%, the microbial composition being devoid of fecal material.

According to an aspect of some embodiments of the present invention there is provided a feed comprising the microbial composition described herein.

According to an aspect of some embodiments of the present invention there is provided a pharmaceutical composition comprising the microbial composition described to herein as the active agent and a pharmaceutically acceptable carrier.

According to an aspect of some embodiments of the present invention there is provided a method of determining whether a ruminating animal associated with a particular phenotype comprising:

(a) analyzing rumen microflora of the animal in order to determine a rumen microbiome signature for the animal; and (b) comparing the rumen microbiome signature of the ruminating animal to one or more rumen microbiome reference signatures, wherein the one or more rumen microbiome reference signatures comprises a positive rumen microbiome reference signature based on results from a control animal associated with the phenotype; wherein when the rumen microbiome signature for the ruminating animal is statistically significantly similar to the positive rumen microbiome reference signature, it is indicative that the ruminating animal is associated with the particular phenotype.

According to an aspect of some embodiments of the present invention there is provided a method of ensuring a high fat milk content in lactating cows comprising administering to the cows a microbial composition comprising a plurality of microbes, the composition having a Firmicutes-to-Bacteroidetes ratio above 1.6, a percent of *Euabacterium* greater than 0.6% and a percent of Lachnospiraceae greater than about 8%, thereby ensuring a high fat milk content in lactating cows.

According to some embodiments of the invention, the phenotype comprises a propensity to infection.

According to some embodiments of the invention, the phenotype comprises fertility.

According to some embodiments of the invention, the composition is devoid of fecal material.

According to some embodiments of the invention, the phenotype comprises milk production.

According to some embodiments of the invention, the phenotype comprises meat quality.

According to some embodiments of the invention, the phenotype comprises milk quality.

According to some embodiments of the invention, the phenotype comprises milk quantity.

According to some embodiments of the invention, the milk quality is selected from the group consisting of a fat content, a lactose content and a protein content.

According to some embodiments of the invention, the infection is selected from the group consisting of brucellosis, campylobacteriosis, cryptosporidiosis, mastitis, *Escherichia coli* 0157:H7, Q Fever (*Coxiella burnetti*) infection and *Salmonella* infection.

According to some embodiments of the invention, the administering is effected more than one time.

According to some embodiments of the invention, the second ruminating animal is a newborn.

According to some embodiments of the invention, the second ruminating animal is not older than one month.

According to some embodiments of the invention, the microbial composition is comprised in a feed.

According to some embodiments of the invention, the microbial composition is comprised in a silage.

According to some embodiments of the invention, the microbial composition is comprised in an enema.

According to some embodiments of the invention, the second ruminating animal is treated with an antibiotic composition prior to the administering.

According to some embodiments of the invention, less than 50% of the microbial composition are of the bacteroidetes phylum.

According to some embodiments of the invention, less than 50% of the microbial composition are of the *prevotella* species, wherein more than 0.4% of the microbial composition are of the *Eubacteria* species and more than 7% of the microbial composition are or the *Lachnospiracae* species.

According to some embodiments of the invention, the ruminating animal is a cow.

According to some embodiments of the invention, the cow comprises a lactating cow.

According to some embodiments of the invention, less than 50% of the microbial composition are of the bacteroidetes phylum.

According to some embodiments of the invention, less than 50% of the microbial composition are of the *prevotella* species, wherein more than 0.4% of the microbial composition are of the *Eubacteria* species and more than 7% of the microbial composition are of the *Lachnospiracae* species.

According to some embodiments of the invention, the method further comprises comparing the rumen microbiome signature of the ruminating animal with a negative rumen microbiome reference signature based on results from a control animal not associated with the phenotype, wherein when the rumen microbiome signature for the animal is statistically significantly similar to the negative rumen microbiome reference signature, it is indicative that the ruminating animal is not is associated with the particular phenotype.

According to some embodiments of the invention, the statistical significance has a P value of 0.05 or less.

According to some embodiments of the invention, the phenotype comprises a propensity to infection.

According to some embodiments of the invention, the phenotype comprises fertility.

According to some embodiments of the invention, the phenotype comprises milk production.

According to some embodiments of the invention, the phenotype comprises meat quality.

According to some embodiments of the invention, the phenotype comprises milk quality.

According to some embodiments of the invention, the phenotype comprises milk quantity.

According to some embodiments of the invention, the comparing the rumen microbiome signature comprises comparing a relative abundance of at least one microbe selected from the group consisting of *Prevotella, Eubacterium Lachnospiraceae, Dialister, Lactobacillus, Desulfovibrio, Bifidobacterium* and *Bulleidia, Atopobium, Adlercreutzia, Mitsuokella* and *Desulfovibrio*.

According to some embodiments of the invention, the comparing the rumen microbiome signature comprises comparing a relative abundance of each of *Prevotella, Eubacteria* and *Lachnospiracae*.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
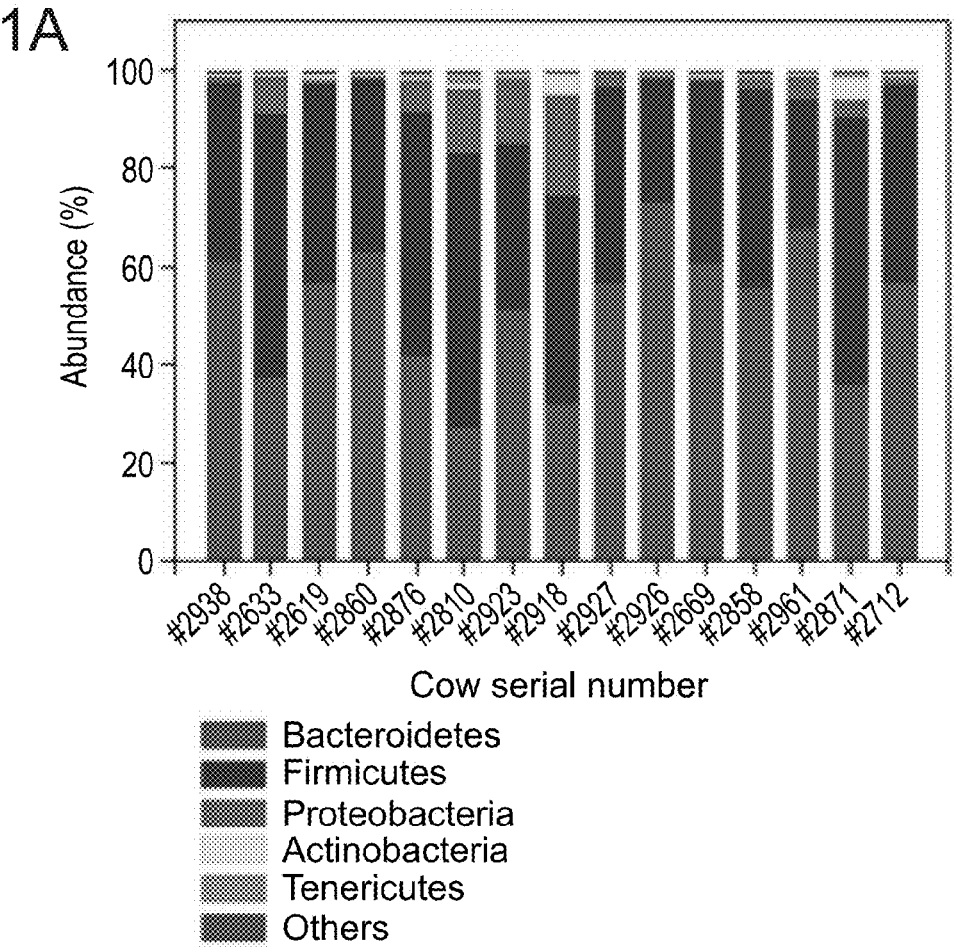
Figure 1B:
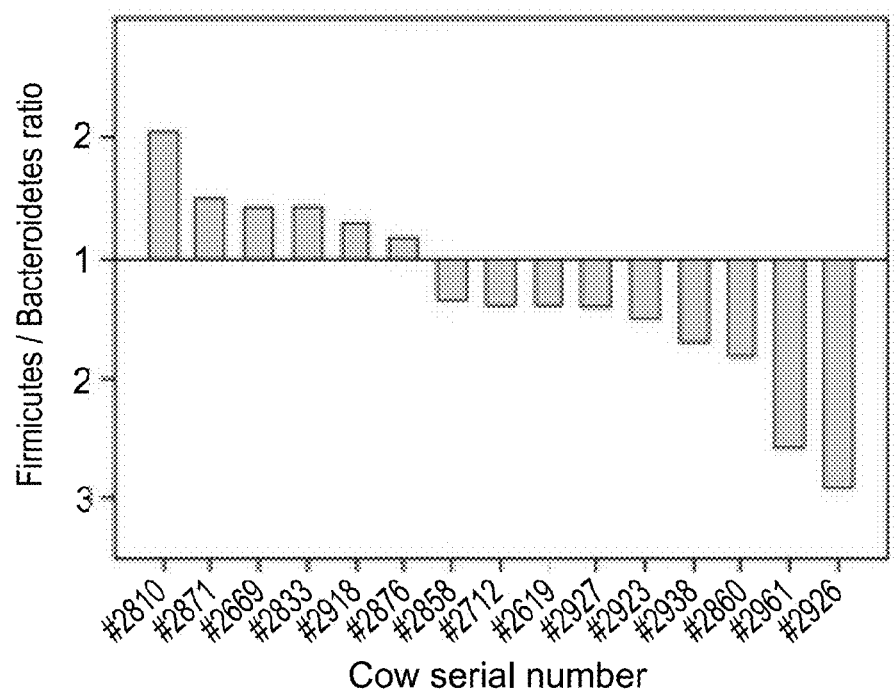

FIGS. 1A-B are graphs illustrating phylum level composition. (A) Stacked bar plot showing the phylum-level composition for each individual cow rumen sampled. (B) Ratio of Firmicutes to Bacteroidetes.

Figure 2:
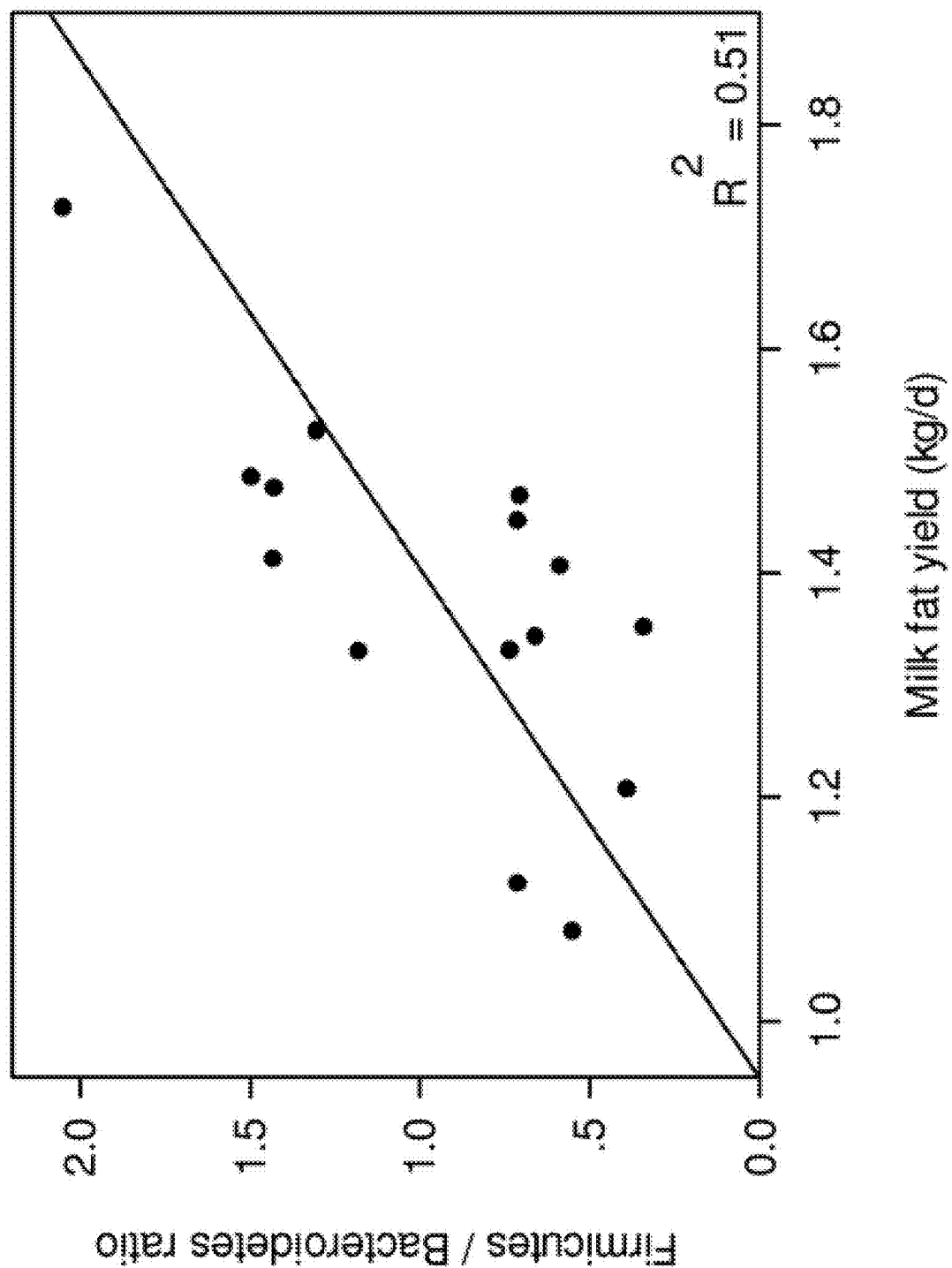

FIG. 2 is a scatter plot illustrating the correlation between milk-fat yield and Firmicutes-to-Bacteroidetes ratio. The plot shows the amount of fat produced per day for each cow (X-axis), vs. the Firmicutes-to-Bacteroidetes ratio. Each point represents one individual cow. $R^2$ of the linear regression is shown in the upper right corner of the plot.

Figure 3:
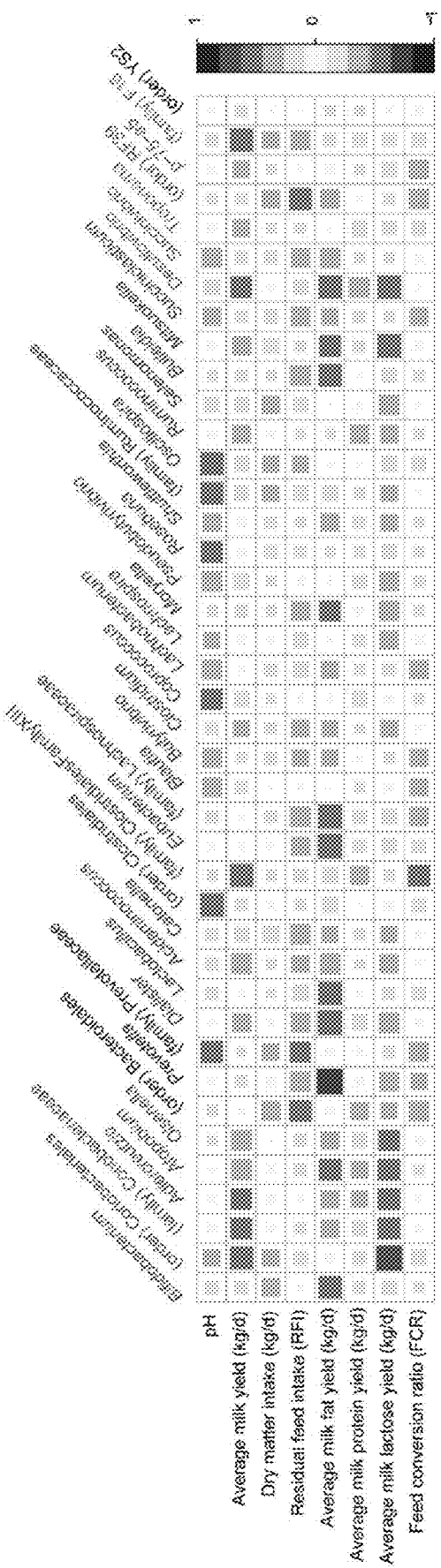

FIG. 3 illustrates the correlation between efficiency parameter and genus abundance. Pearson linear correlation matrix of the dominant bacterial genera across the rumen samples. The genera were added to the matrix if they were in at least 50% of the cows and represented at least 0.1% of the bacterial community in at least one of the cows. Strong correlations are indicated by large squares, whereas weak correlations are indicated by small squares. The colors of the scale denote whether there is a positive correlation (closer to 1, blue squares) or negative correlation (closer to 0, red squares) between the genera and the efficiency parameters. Color coding represents the phylum to which each genus belongs, as follows: Actinobacteria (green), Bacteroidetes (blue), Firmicutes (red), Proteobacteria (orange), Spirochaetes (purple), Tenericutes (light blue), TM7 (olive), Cyanobacteria (black).

Figure 4:
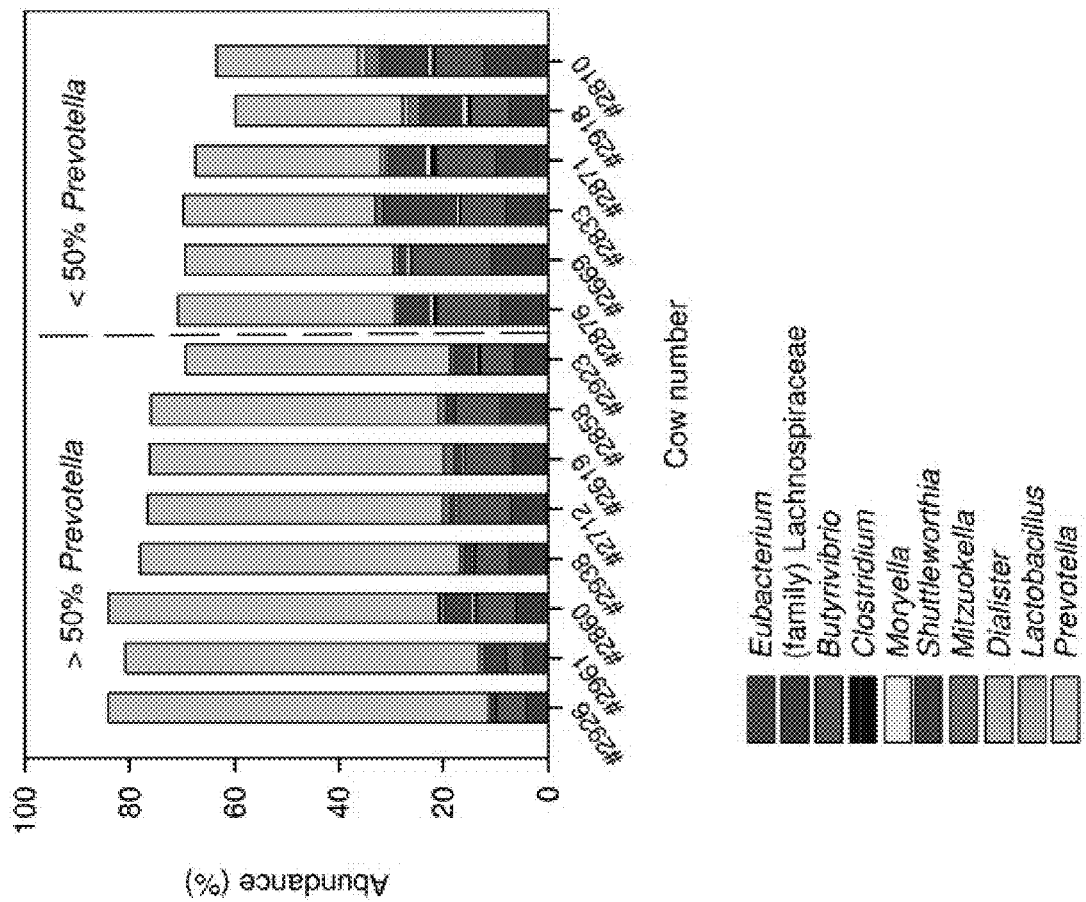

FIG. 4 is a bar graph illustrating the abundance of genera within the phylum Firmicutes compared to the genus *Prevotella*. The graph shows the abundance of genera belonging to the phylum Firmicutes that were negatively correlated with *Prevotella* abundance. These included all genera that were in at least half of the cows samples and constituted 0.1% of the reads in at least one cow. The grey portion of the bars represents the abundance of *Prevotella* (phylum Bacteroidetes). The dashed line separates samples with more than 50% *Prevotella* (left side) and from those with less than 50% *Prevotella*.

Figure 5:
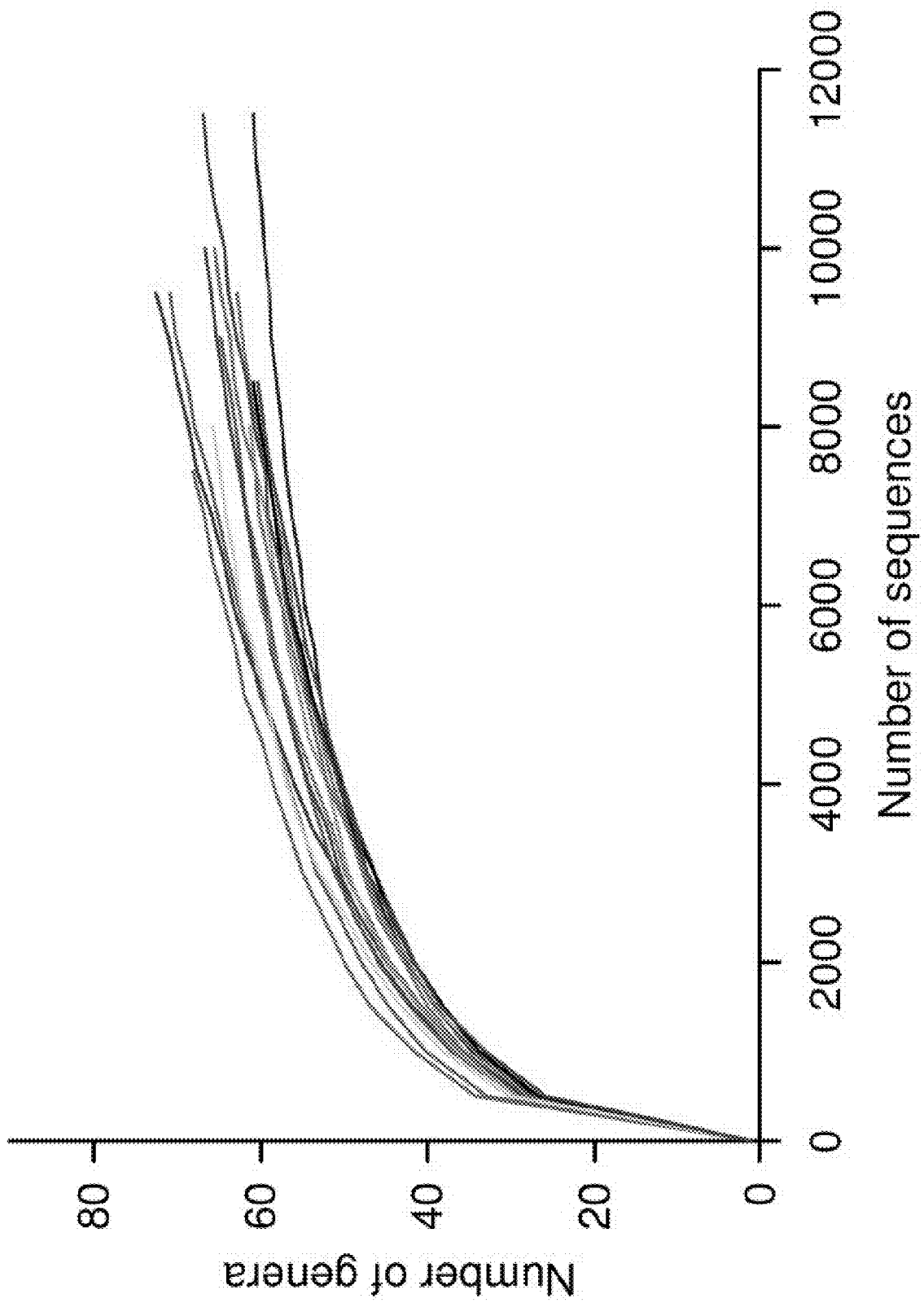

FIG. 5 illustrates genus-level rarefaction curves of rumen microbiota. Rumen microbiota from each of the 15 individual animals were sampled according to their 16S rRNA gene sequences.

Figure 6:
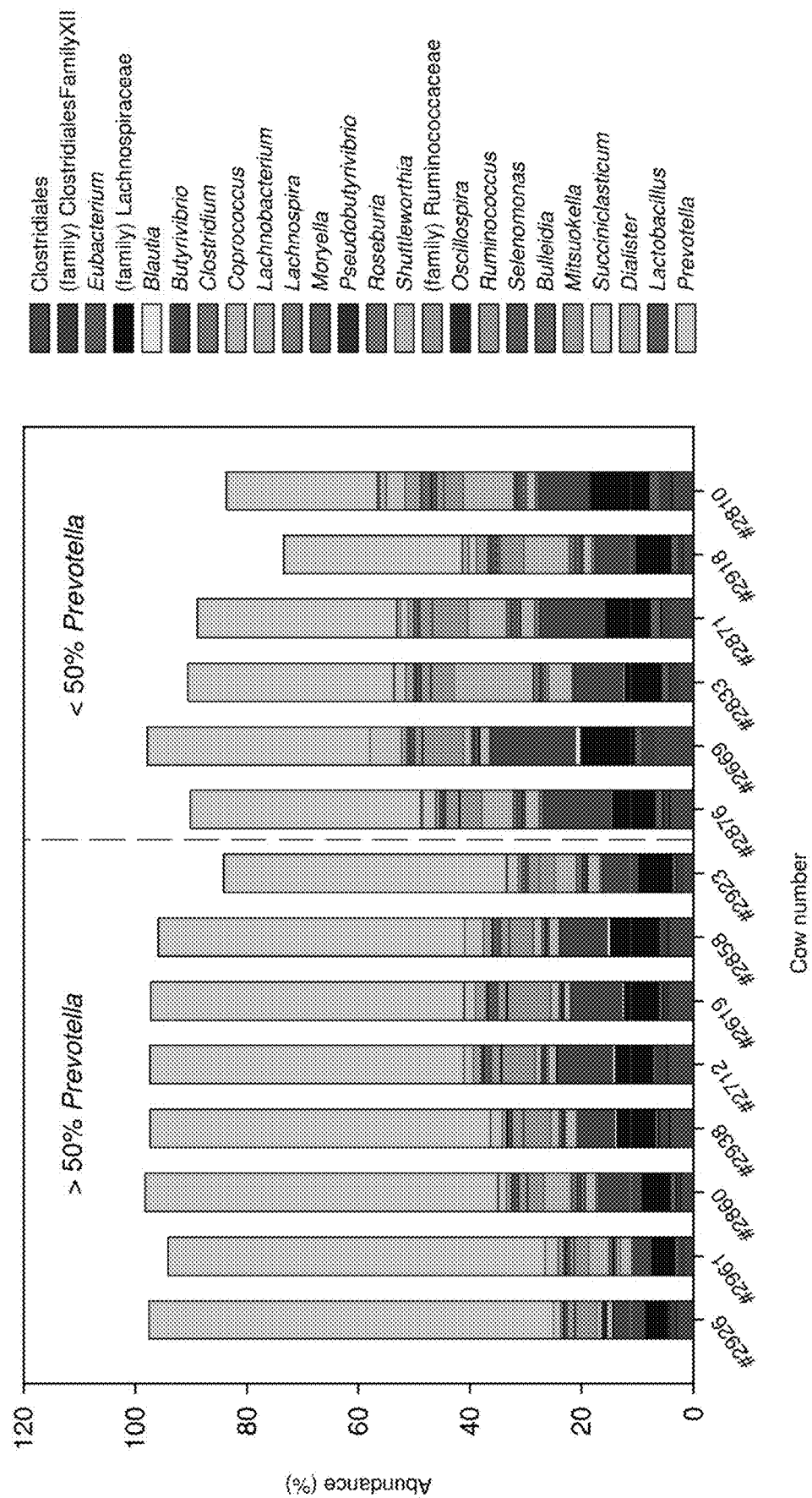

FIG. 6 illustrates the abundance of genera of the phylum Firmicutes compared to the genus *Prevotella*. Stack plot showing the abundance levels of each of the 23 genera belonging to the phylum Firmicutes included in the correlation analyses. These include all genera that were in at least half of the cows sampled and constituted 0.1% of the reads in at least one cow. The gray portion of the bars represents the abundance of *Prevotella* (phylum Bacteroidetes).

Figure 7:
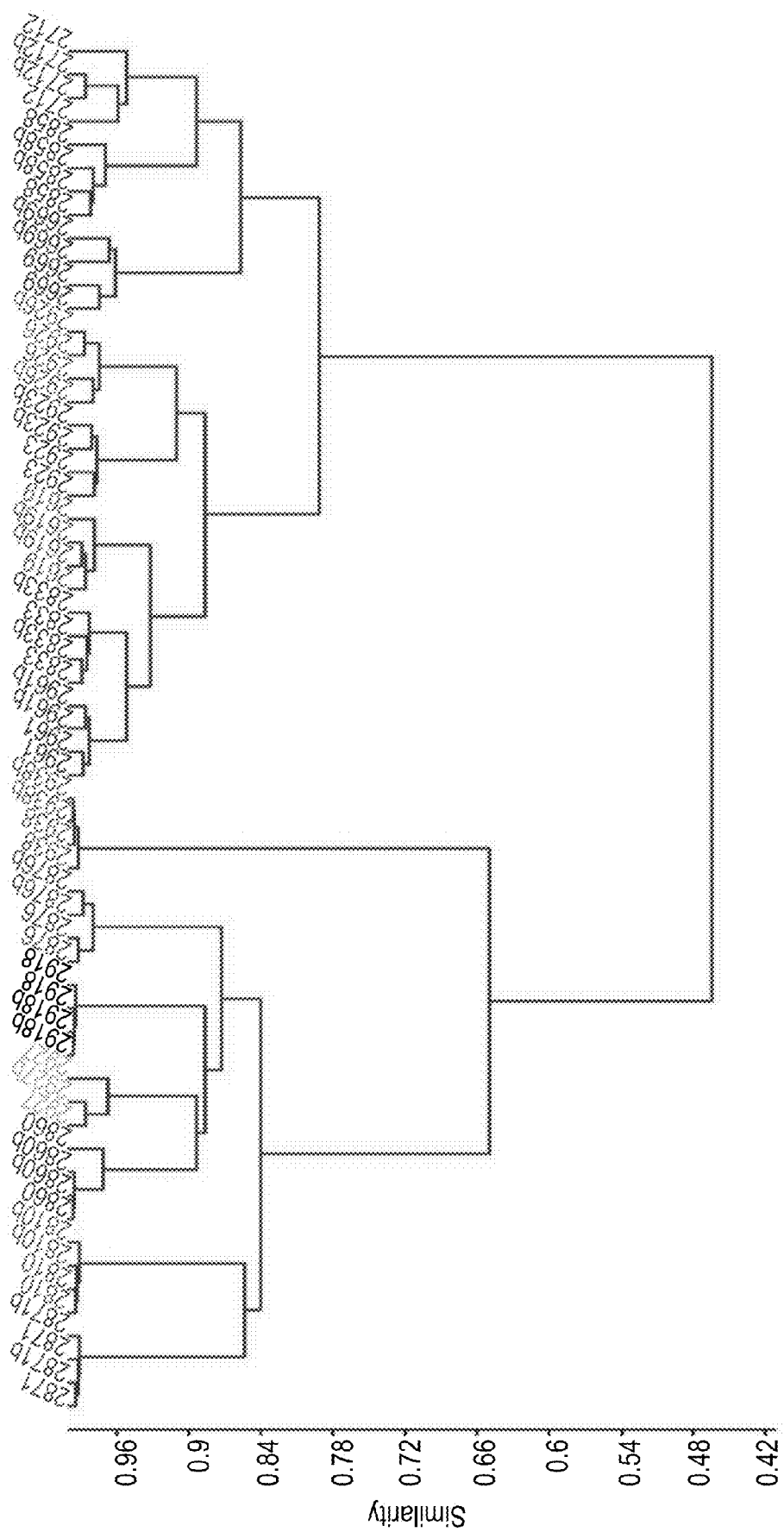

FIG. 7 is an assessment of the robustness of bacterial extraction and DNA purification protocols used in this study. Dendrogram showing the degree of Bray-Curtis similarity between each sample and the technical duplicates for the bacterial extraction and purification protocols. Each animal sampled is represented by a different color. Samples with the same serial designation are the technical PCR duplicates and the ones with the letter "b" added to the same serial number represent the duplicates for the bacterial extraction and purification protocols.

DESCRIPTION OF SPECIFIC EMBODIMENTS OF THE INVENTION

The present invention, in some embodiments thereof, relates to rumen microflora and uses thereof. In one embodiment, the present invention relates to rumen microflora in order to regulate milk production in ruminating animals.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Ruminants are completely dependent on their microbiota for feed digestion and consequently, their viability. The present inventors hypothesized that a connection between the composition and abundance of resident rumen bacterial taxa and the physiological parameters of the host may exist. Using a pyrosequencing approach, they characterized the rumen bacterial community composition in 15 dairy cows and their physiological parameters. They analyzed the degree of divergence between the different animals and found that some physiological parameters, such as milk yield and composition, are highly correlated with the abundance of various bacterial members of the rumen microbiome. One apparent finding was a strong correlation between the ratio of the phyla Firmicutes to Bacteroidetes and milk-fat yield. These findings paralleled human studies showing similar trends of increased adiposity with an increase in Bacteroidetes. This correlation remained evident at the genus level, where several genera showed correlations with the animals' physiological parameters. This suggests that the bacterial community has a role in shaping host physiological parameters. Thus, the present inventors propose that it is possible to mimic physiological traits by modulation of the rumen microbiome.

Thus, according to one aspect of the present invention there is provided a method of mimicking a phenotype of a first ruminating animal in a second ruminating animal comprising administering to the second ruminating animal a microbial composition comprising a plurality of microbes having a signature which is statistically significantly similar to the microbial signature of a rumen microbiome of the first ruminating animal, wherein the first and the second ruminating animal are of identical species, thereby mimicking the phenotype of the first ruminating animal in the second ruminating animal.

Ruminating animals contemplated by the present invention include for example cattle (e.g. cows), goats, sheep, giraffes, American Bison, European Bison, yaks, water buffalo, deer, camels, alpacas, llamas, wildebeest, antelope, pronghorn, and nilgai.

One exemplary phenotype that the present invention contemplates that may be mimicked in a ruminating animal is a propensity (i.e. likelihood) to a disease. The present invention contemplates that by providing the microbial composition described herein, it may be possible to avoid or delay the development of a disease or condition and/or lessen the associated symptoms. In some embodiments, the treated animal may already exhibit overtly one or more symptoms of a disease/condition of interest. In other embodiments, the treated animal may be asymptomatic with respect to a disease or condition of interest, but for some reason, may be deemed susceptible to developing the disease or condition. In other embodiments, the animal is healthy.

According to one example, the disease is an infectious disease. For example if a ruminating animal shows a lower propensity to infection than the average propensity to infection amongst that animal, it may be desirable to mimic this trait in additional animals of the same species.

Non-limiting examples of infections for which it may be desirable to mimic predisposition to include any one of brucellosis, campylobacteriosis, cryptosporidiosis, mastitis, *Escherichia coli* 0157:H7, Q Fever (*Coxiella burnetti*) infection and *Salmonella* infection.

Another exemplary phenotype that the present invention contemplates that may be mimicked in a ruminating animal is fertility. Thus, for a male animal which is especially virile, (i.e. more so than the average virility of males animals of the same species) it may be desirable to mimic this trait in additional male animals. Correspondingly, for a female animal which shows a higher ability to be impregnated than the average impregnation rate of other female animals of the same species), it may also be desirable to mimic this trait in additional female animals.

Another exemplary phenotype that the present invention contemplates that may be mimicked in a ruminating animal is milk production. Thus, for a female animal (e.g. cow) that produces a higher quantity of milk than the average amount of milk produced by cows fed on the same diet, it may be desirable to mimic this trait in additional cows.

Additionally, or alternatively, for a female animal (e.g. cow) that produces milk to of higher quality (e.g. fat content) than the milk produced by cows fed on the same diet, it may be desirable to mimic this trait in additional cows. Other contemplated phenotypes concerning milk production that may be mimicked include production of milk having a higher than average lactate content and/or production of milk having a higher than average protein content.

Still another exemplary phenotype that the present invention contemplates that may be mimicked in a ruminating animal is quality of meat production. Thus, for example if an animal shows a higher muscle:fat ratio than the average muscle:fat ratio of animals fed on the same diet, it may be desirable to mimic this trait in additional animals.

The present invention contemplates altering the phenotype of ruminating animals of all ages. According to a particular embodiment, the animals whose phenotype is altered are newborns, typically not more than one day old. According to another embodiment, the animals are not more than two days old. According to another embodiment, the animals are not more than three days old. According to another embodiment, the animals are not more than 1 week old. According to another embodiment, the animals are not more than 2 week old. According to another embodiment, the animals are not more than 1 month old. According to another embodiment, the animals are not more than 3 months old. According to still another embodiment, the animals are adult.

As mentioned, the present invention contemplates providing ruminating animals with microbial compositions which comprise a plurality of microbes having a signature which is statistically significantly similar to a rumen microbiome of a ruminating animal which has an advantageous phenotype or trait.

As used herein, the term "microbiome" refers to the totality of microbes (bacteria, fungae, protists), their genetic elements (genomes) in a defined environment, e.g. within the rumen of a host.

The microbial compositions of the present invention may comprise more than 10 species of microbes, 20 species of microbes, 30 species of microbes, 40 species of microbes, 50 species of microbes, 60 species of microbes, 70 species of microbes, 80 species of microbes, 90 species of microbes, 100 species of microbes, 200 species of microbes, 300 species of microbes, 400 species of microbes, more than 500 species of microbes or more than 1000 species of microbes.

According to a particular embodiment, the composition comprises between 10-10,000 species of microbes, between 100-10,000 species of microbes or between 1000-10,000 species of microbes.

The present invention encompasses the recognition that microbial signatures can be relied upon as proxy for microbiome composition and/or activity. Microbial signatures comprise data points that are indicators of microbiome composition and/or activity. Thus, according to the present invention, changes in microbiomes can be detected and/or analyzed through detection of one or more features of microbial signatures.

In some embodiments, a microbial signature includes information relating to absolute amount of one or more types of microbes, and/or products thereof. In some embodiments, a microbial signature includes information relating to relative amounts of five, ten, twenty or more types of microbes and/or products thereof.

In some embodiments, a microbial signature includes information relating to presence, level, and/or activity of at least ten types of microbes. In some embodiments, a microbial signature includes information relating to presence, level, and/or activity of between 5 and 100 types of microbes. In some embodiments, a microbial signature includes information relating to presence, level, and/or activity of between 100 and 1000 or more types of microbes. In some embodiments, a microbial signature includes information relating to presence, level, and/or activity of substantially all types of microbes within the microbiome.

In some embodiments, a microbial signature comprises a level or set of levels of five, or ten or more types of microbes or components or products thereof. In some embodiments, a microbial signature comprises a level or set of levels of five or ten or more DNA sequences. In some embodiments, a microbial signature comprises a level or set of levels of ten or more 16S rRNA gene sequences. In some embodiments, a microbial signature comprises a level or set of levels of 18S rRNA gene sequences. In some embodiments, a microbial signature comprises a level or set of levels of five or ten or more RNA transcripts. In some embodiments, a microbial signature comprises a level or set of levels of five or ten or more proteins. In some embodiments, a microbial signature comprises a level or set of levels of five or ten or more metabolites.

16S and 18S rRNA gene sequences encode small subunit components of prokaryotic and eukaryotic ribsosomes respectively. rRNA genes are particularly useful in distinguishing between types of microbes because, although sequences of these genes differs between microbial species, the genes have highly conserved regions for primer binding. This specificity between conserved primer binding regions allows the rRNA genes of many different types of microbes to be amplified with a single set of primers and then to be distinguished by amplified sequences.

According to one embodiment of this aspect of the present invention two microbiomes have a statistically significant similar signature when they comprise at least 50% of the same microbes, at least 60% of the same microbes, at least 70% of the same microbes, at least 80% of the same microbes, at least 90% of the same microbes, at least 91% of the same microbes, at least 92% of the same microbes, at least 93% of the same microbes, at least 94% of the same microbes, at least 95% of the same microbes, at least 96% of the same microbes, at least 97% of the same microbes, at least 98% of the same microbes, at least 99% of the same microbes or 100% of the same microbes.

According to another embodiment, in order to classify a microbe as belonging to a particular genus, it must comprise at least 90% sequence homology, at least 91% sequence homology, at least 92% sequence homology, at least 93% sequence homology, at least 94% sequence homology, at least 95% sequence homology, at least 96% sequence homology, at least 97% sequence homology, at least 98% sequence homology, at least 99% sequence homology to a reference microbe known to belong to the particular genus. According to a particular embodiment, the sequence homology is at least 95%.

According to another embodiment, in order to classify a microbe as belonging to a particular species, it must comprise at least 90% sequence homology, at least 91% sequence homology, at least 92% sequence homology, at least 93% sequence homology, at least 94% sequence homology, at least 95% sequence homology, at least 96% sequence homology, at least 97% sequence homology, at least 98% sequence homology, at least 99% sequence homology to a reference microbe known to belong to the particular species. According to a particular embodiment, the sequence to homology is at least 97%.

Additionally, or alternatively, microbiomes may have a statistically significant similar signature when the quantity (e.g. occurrence) in the microbiome of at least one microbe of interest is identical. According to another embodiment, microbiomes may have a statistically significant similar signature when the relative ratio in the microbiome of at least 10% of its microbes are identical. According to another embodiment, microbiomes may have a statistically significant similar signature when the relative ratio in the microbiome of at least 20% of its microbes are identical. According to another embodiment, microbiomes may have a statistically significant similar signature when the relative ratio in the microbiome of at least 30% of its microbes are identical. According to another embodiment, microbiomes may have a statistically significant similar signature when the relative ratio in the microbiome of at least 40% of its microbes are identical. According to another embodiment, microbiomes may have a statistically significant similar signature when the relative ratio in the microbiome of at least 50% of its microbes are identical. According to another embodiment, microbiomes may have a statistically significant similar signature when the relative ratio in the microbiome of at least 60% of its microbes are identical. According to another embodiment, microbiomes may have a statistically significant similar signature when the relative ratio in the microbiome of at least 70% of its microbes are identical. According to another embodiment, microbiomes may have a statistically significant similar signature when the relative ratio in the microbiome of at least 80% of its microbes are identical. According to another embodiment, microbiomes may have a statistically significant similar signature when the relative ratio in the microbiome of at least 90% of its microbes are identical. Thus, the fractional percentage of microbes (e.g. relative amount, ratio, distribution, frequency, percentage, etc.) of the total may be statistically similar.

The present inventors have deduced a signature of a microbial composition which is particularly effective at enhancing the percentage of fat in milk of lactating animals.

Thus, a microbial composition which comprises a Firmicutes-to-Bacteroidetes ratio above about 1 is effective for increasing the amount of fat produced per day in milk of lactating animals to a quantity of about 1.4 kg. A microbial composition which comprises a Firmicutes-to-Bacteroidetes ratio above about 1.5 is effective for increasing to the amount of fat produced per day in milk of lactating animals to a quantity of about 1.6 kg. A microbial composition which comprises a Firmicutes-to-Bacteroidetes ratio above about 1.6 is effective for increasing the amount of fat produced per day in milk of lactating animals to a quantity of about 1.8 kg.

The amount of *prevotella* (the dominant Bacteroidetes) may be used to estimate the Firmicutes-to-Bacteroidetes. The lower the amount of *prevotella* in the microbial composition, typically the higher the amount of fat present in the milk.

Additionally, the amount of *Eubacterium* in the microbial composition correlates with milk fat production. When the percent of *Eubacterium* in the composition is greater than about 0.4%, the amount of fat produced in milk of lactating animals is typically about 1.4 kg per day. When the percent of *Eubacterium* in the composition is greater than about 0.5%, the amount of fat produced in milk of lactating animals is typically about 1.6 kg per day. When the percent of *Eubacterium* in the composition is greater than about 0.6%, the amount of fat produced in milk of lactating animals is typically about 1.8 kg per day.

Additionally, the amount of Lachnospiraceae in the microbial composition correlates with milk fat production. When the percent of Lachnospiraceae in the composition is greater than about 8%, the amount of fat produced in milk of lactating animals is typically about 1.5 kg per day. When the percent of Lachnospiraceae in the composition is greater than about 10%, the amount of fat produced in milk of lactating animals is typically about 1.8 kg per day.

Thus, the present invention contemplates microbial compositions having a Firmicutes-to-Bacteroidetes ratio above 1.5 (e.g. 1.5, 1.6, 1.7 1.8), a percent of *Eubacterium* greater than 0.6% (e.g. 0.6, 0.7, 0.8) and a percent of Lachnospiraceae greater than about 8% (e.g. 8, 9, 10) for increasing fat content in lactating cows.

Additional microbial compositions contemplated by the present invention include those where about 50% of the microbial composition are of the *prevotella* species, wherein more than about 0.4% of the microbial composition are of the *Eubacteria* species and more than about 7% of the microbial composition are or the *Lachnospiracae* species.

Microbial compositions wherein between 40-60% of the microbes are *prevotella*, 0.4-0.8% of the microbes are *Eubacteria* and 6-10% of the microbes are *Lachnospiracae*.

The genus *Dialister* was also shown to correlate with milk fat production, as was *Lactobacillus, Desulfovibrio, Bifidobacterium* and *Bulleidia*, Significant positive correlations were observed between Atopobium, Adlercreutzia and two unknown genera belonging to the order Coriobacteriales and milk-lactose content. In addition, both *Mitsuokella* and *Desulfovibrio* were positively correlated with milk-lactose yield.

Thus microbial compositions are contemplated which comprises at least one, at least two, at least three, at least four, at least five, at least six, at least seven, at least, eight, at least nine, at least ten of the above mentioned species in any combination.

In another embodiment, the microbial compositions comprises at least one, at least two, at least three, at least four, at least five, at least six, at least seven, at least, eight, at least nine, at least ten, at least 11, at least 12, at least 13, at least 14, at least 15, at least 16, at least 17, at least 18, at least 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 or 53 of the following list of microbes: *Lactobacillus, Acidaminococcus, Bifidobacterium, Dialister,* RF39, *Olsenella,* (family) Prevotellaceae, *Catonella, Treponema,*

(order) Coriobacteriales, (family) Coriobacteriaceae, *Adlercreutzia*, *Atopobium*, (order) Bacteroidales, *Prevotella*, (order) YS2, (order) Clostridiales, family Clostridiales, *Eubacterium*, (family) Lachnospiraceae, *Blautia, Butyrivibrio, Clostridium, Coprococcus, Lachnobacterium, Lachnospira, Moryella, Pseudobutyrivibrio, Roseburia, Shuttleworthia*, (family) Ruminococcaceae, *Oscillospira, Ruminococcus, Selenomonas, Desulfovibrio*, (order) Aeromonadales, family F16, *Bulleidia*, p-75-a5, *Mitsuokella* and *succiniclasticum*.

The microbial compositions of this aspect of the present invention are typically derived from a microbiota sample of the rumen.

A microbiota sample comprises a sample of microbes and or components or products thereof from a microbiome.

In some embodiments, a microbiota sample is collected by any means that allows recovery of microbes or components or products thereof of a microbiome and is appropriate to the relevant microbiome source i.e. rumen.

Rumen may be collected using methods known in the art and include for example use of a stomach tube with a rumen vacuum sampler. Typically rumen is collected after feeding.

The animals from which the rumen is collected may be newborn animals, young animals (less than one month old) or fully adult animals.

The microbial composition may be derived directly from a microbiota sample of the animal having an advantageous phenotype. Alternatively, the microbial composition may be artificially created by adding known amounts of different microbes. It will be appreciated that the microbial composition which is derived from the microbiota sample of an animal may be manipulated prior to administrating by increasing the amount of a particular strain or depleting the amount of a particular strain. Preferably, the microbial compositions are not treated in any way which serves to alter the relative balance between the microbial species and taxa comprised therein.

In some embodiments, the microbial composition is expanded ex vivo using known culturing methods prior to administration. In other embodiments, the microbial composition is not expanded ex vivo prior to administration.

According to one embodiment, the microbial composition is not derived from fecal material.

According to still another embodiment, the microbial composition is devoid (or comprises only trace quantities) of fecal material (e.g. fiber).

Prior to administration, the animal may be pretreated with an agent which reduces the number of naturally occurring rumen microbiome (e.g. by antibiotic treatment). According to a particular embodiment, the treatment significantly eliminates the naturally occurring rumen microflora by at least 20%, 30% 40%, 50%, 60%, 70%, 80% or even 90%.

The microbial composition may be administered per se (e.g. using a catheter or syringe) or may be administered together in the feed (e.g. as a feed additive) of the animal or the drink of the animal.

These ruminants may be fed the feed additive composition of the present invention at any time and in any amount during their life. That is, the ruminant may be fed the feed additive composition of the present invention either by itself or as part of a diet which includes other feedstuffs. Moreover, the ruminant may be fed the feed additive composition of the present invention at any time during their lifetime. The ruminant may be fed the feed additive composition of the present invention to continuously, at regular intervals, or intermittently. The ruminant may be fed the feed additive composition of the present invention in an amount such that it accounts for all, a majority, or a minority of the feed in the ruminant's diet for any portion of time in the animal's life. According to one embodiment, the ruminant is fed the feed additive composition of the present invention in an amount such that it accounts for a majority of the feed in the animal's diet for a significant portion of the animal's lifetime.

Examples of additional rumen active feed additives which may be provided together with the feed additive of the present invention include buffers, fermentation solubles, essential oils, surface active agents, monensin sodium, organic acids, and supplementary enzymes.

Also contemplated is encapsulation of the microbes in nanoparticles or microparticles using methods known in the art including those disclosed in EP085805, EP1742728 A1, WO2006100308 A2 and U.S. Pat. No. 8,449,916, the contents of which are incorporated by reference.

The compositions may be administered orally, rectally or any other way which is beneficial to the animal such that the microbes reach the rumen of the animal.

In another embodiment, the present invention provides novel processes for raising a ruminant by feeding the ruminant such a feed additive composition. Such ruminants include cattle, goats, sheep, giraffes, American Bison, European Bison, yaks, water buffalo, deer, camels, alpacas, llamas, wildebeest, antelope, pronghorn, and nilgai.

In another embodiment, the present invention provides novel processes for making milk by harvesting milk from a ruminant which have been fed such a feed additive composition. The ruminants in this embodiment are those which produce milk, such as cattle, oxen, bison, deer, goats, sheep, etc. The feeding may be carried out as described above in connection with the process for raising ruminants. The harvesting of the milk may be carried out using the conventional techniques known to those in the art. The milk may be processed, stored, cooled, shipped, and packaged, as described in Kirk-Othmer, Encyclopedia of Chemical Technology, Fourth Ed., Wiley-Interscience, NY, vol. 16, pp. 700-746, 1995, which is incorporated herein by reference.

In another embodiment, the present invention provides processes for making a dairy product from the milk harvested from a ruminant which has been fed the feed additive composition of the present invention. Such dairy products include evaporated and condensed milk, dry milk, cream, anhydrous milk fat, butter, buttermilk, cheese, yogurt, and frozen desserts (such as ice cream, frozen yogurt, ice milk, sherbets, and mellorine), lactose, and casein. The conversion of the milk into the dairy product may be carried out using conventional techniques known to those skilled in the art as described in Kirk-Othmer, Encyclopedia of Chemical Technology, Fourth Ed., Wiley-Interscience, NY, vol. 16, pp. 700-746, 1995, which is incorporated herein by reference.

According to one embodiment, the microbial composition is formulated as a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the microbes of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. The physiologically acceptable carrier is selected such that the microbes remain viable.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically to acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in context of the present invention include compositions wherein the active ingredients are contained in an amount effective to achieve the intended purpose. More specifically, a therapeutically effective amount means an amount of active ingredients (microbes) effective to prevent, alleviate or ameliorate symptoms of a disorder (e.g., infectious disease) or prolong the survival of the animal being treated.

Determination of a therapeutically effective amount is well within the capability of those skilled in the art, especially in light of the detailed disclosure provided herein.

Dosage amount and interval may be adjusted individually to provide microbe numbers sufficient to induce an effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the animal being treated (e.g. age, weight) and the manner of administration.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a to compatible pharmaceutical carrier may also be prepared, placed in an appropriate container, and labeled for treatment of an indicated condition, as if further detailed above.

According to another aspect of the present invention there is provided a method of determining whether a ruminating animal is associated with a particular phenotype comprising:

(a) analyzing rumen microflora of the animal in order to determine a rumen microbiome signature for the animal; and (b) comparing the rumen microbiome signature of the ruminating animal to one or more rumen microbiome reference signatures, wherein the one or more rumen microbiome reference signatures comprises a positive rumen microbiome reference signature based on results from a control animal associated with the phenotype; wherein when the rumen microbiome signature for the ruminating animal is statistically significantly similar to the positive rumen microbiome reference signature, it is indicative that the ruminating animal is associated with the particular phenotype. The rumen microflora may be analyzed on a quantitative level and/or a qualitative level.

Methods of quantifying levels of microbes of various types are described herein below.

In some embodiments, determining a level or set of levels of one or more types of microbes or components or products thereof comprises determining a level or set of levels of one or more DNA sequences. In some embodiments, one or more DNA sequences comprises any DNA sequence that can be used to differentiate between different microbial types. In certain embodiments, one or more DNA sequences comprises 16S rRNA gene sequences. In certain embodiments, one or more DNA sequences comprises 18S rRNA gene sequences. In some embodiments, 1, 2, 3, 4, 5, 10, 15, 20, 25, 50, 100, 1,000, 5,000 or more sequences are amplified.

In some embodiments, a microbiota sample is directly assayed for a level or set of levels of one or more DNA sequences. In some embodiments, DNA is isolated from a microbiota sample and isolated DNA is assayed for a level or set of levels of one or more DNA sequences. Methods of isolating microbial DNA are well known in the art. Examples include but are not limited to phenol-chloroform extraction and a wide variety of commercially available kits, including QJAamp DNA Stool Mini Kit (Qiagen, Valencia, Calif.).

In some embodiments, a level or set of levels of one or more DNA sequences is determined by amplifying DNA sequences using PCR (e.g., standard PCR, semi-quantitative, or quantitative PCR). In some embodiments, a level or set of levels of one or more DNA sequences is determined by amplifying DNA sequences using quantitative PCR. These and other basic DNA amplification procedures are well known to practitioners in the art and are described in Ausebel et al. (Ausubel F M, Brent R, Kingston R E, Moore D D, Seidman J G, Smith J A, Struhl K (eds). 1998. Current Protocols in Molecular Biology. Wiley: New York).

In some embodiments, DNA sequences are amplified using primers specific for one or more sequence that differentiate(s) individual microbial types from other, different microbial types. In some embodiments, 16S rRNA gene sequences or fragments thereof are amplified using primers specific for 16S rRNA gene sequences. In some embodiments, 18S DNA sequences are amplified using primers specific for 18S DNA sequences.

In some embodiments, a level or set of levels of one or more 16S rRNA gene sequences is determined using phylochip technology. Use of phylochips is well known in the art and is described in Hazen et al. ("Deep-sea oil plume enriches indigenous oil-degrading bacteria." Science, 330, 204-208, 2010), the entirety of which is incorporated by reference. Briefly, 16S rRNA genes sequences are amplified and labeled from DNA extracted from a microbiota sample.

Amplified DNA is then hybridized to an array containing probes for microbial 16S rRNA genes. Level of binding to each probe is then quantified providing a sample level of microbial type corresponding to 16S rRNA gene sequence probed. In some embodiments, phylochip analysis is performed by a commercial vendor. Examples include but are not limited to Second Genome Inc. (San Francisco, Calif.).

In some embodiments, determining a level or set of levels of one or more types of microbes or components or products thereof comprises determining a level or set of levels of one or more microbial RNA molecules (e.g., transcripts). Methods of quantifying levels of RNA transcripts are well known in the art and include but are not limited to northern analysis, semi-quantitative reverse transcriptase PCR, quantitative to reverse transcriptase PCR, and microarray analysis. These and other basic RNA transcript detection procedures are described in Ausebel et al. (Ausubel F M, Brent R, Kingston R E, Moore D D, Seidman J G, Smith J A, Struhl K (eds). 1998. Current Protocols in Molecular Biology. Wiley: New York).

In some embodiments, determining a level or set of levels of one or more types of microbes or components or products thereof comprises determining a level or set of levels of one or more microbial proteins. Methods of quantifying protein levels are well known in the art and include but are not limited to western analysis and mass spectrometry. These and all other basic protein detection procedures are described in Ausebel et al. (Ausubel F M, Brent R, Kingston R E, Moore D D, Seidman J G, Smith J A, Struhl K (eds). 1998. Current Protocols in Molecular Biology. Wiley: New York). In some embodiments, determining a level or set of levels of one or more types of microbes or components or products thereof comprises determining a level or set of levels of one or more microbial metabolites. In some embodiments, levels of metabolites are determined by mass spectrometry. In some embodiments, levels of metabolites are determined by nuclear magnetic resonance spectroscopy. In some embodiments, levels of metabolites are determined by enzyme-linked immunosorbent assay (ELISA). In some embodiments, levels of metabolites are determined by colorimetry. In some embodiments, levels of metabolites are determined by spectrophotometry.

In some embodiments, what is determined is the distribution of microbial families within the microbiome. However, characterization may be carried to more detailed levels, e.g. to the level of genus and/or species, and/or to the level of strain or variation (e.g. variants) within a species, if desired (including the presence or absence of various genetic elements such as genes, the presence or absence of plasmids, etc.).

Alternatively, higher taxonomic designations can be used such as Phyla, Class, or Order. The objective is to identify which microbes (usually bacteria, but also optionally fungi (e.g. yeasts), protists, etc.) are present in the sample from the ruminating animal and the relative distributions of those microbes, e.g. expressed as a percentage of the total number of microbes that are present, thereby establishing a micro floral pattern or signature for the animal being tested, e.g. for the region of the rumen that has been sampled.

Once an individual animal's "signature" with respect to the targeted microbes has been determined, it is compared to known signatures obtained previously from control experiments. Such control experiments typically obtain "positive control" data from animals which are positive for a particular phenotype at the time of the analysis. Based on a comparative analysis between the animal signature and one or more reference or control signatures (and usually corroborated statistically by methods that are well-known to those of ordinary skill in the art) the similarity between the two can be analyzed. For example, an animal with a signature that is not similar to or within the range of values seen in negative control signatures, but which is more similar to or within ranges determined for positive controls, may be deemed to be having that phenotype. This is generally the case, for example, if its level or amount of at least one correlatable microbe is associated with the phenotype with a statistically significant (P value) of less than about 0.05.

In other embodiments of the invention, when many taxa are being considered, the overall pattern of microflora is assessed, i.e. not only are particular taxa identified, but the percentage of each constituent taxon is taken in account, in comparison to all taxa that are detected and, usually, or optionally, to each other. Those of skill in the art will recognize that many possible ways of expressing or compiling such data exist, all of which are encompassed by the present invention. For example, a "pie chart" format may be used to depict a microfloral signature; or the relationships may be expressed numerically or graphically as ratios or percentages of all taxa detected, etc. Further, the data may be manipulated so that only selected subsets of the taxa are considered (e.g. key indicators with strong positive correlations). Data may be expressed, e.g. as a percentage of the total number of microbes detected, or as a weight percentage, etc.

In one embodiment, a nonparametric multivariate test such as Metastats, Analysis of Similarity, Principle Component Analysis, Non-Parametric MANOVA (Kruskal-Wallace) etc. can be used to associate a microbiome signature with a particular phenotype with a statistical significant (P value) of less than 0.05. Such tests are known in the art and are described, for example, by White J R, Nagaraj an N, Pop M (2009) Statistical Methods for Detecting Differentially Abundant Features in Clinical Metagenomic Samples. PLoS Computational Biology 5(4): 1-1 1; and Clarke K R, Gorley R N (2001) PRIMER v5: User Manual and Tutorial, PRIMER-E Ltd. Plymouth Marine Laboratory, UK.

In other embodiments, phylogenetic methods such as Unifrac can be used to associate microbiome signature with a particular phenotype with a statistically significant (P value) of less than 0.05. See, for example, Lozupone C, Knight R (2005) UniFrac: a new phylogenetic method for comparing microbial communities. Appl Environ Microbiol 71:8228-8235.

In other embodiments, support vector machines can be used to associate microbiome signature with a particular phenotype with sufficiently high classification measure (F-measure) and appropriate sensitivity and specificity that is accepted in the state of the art. See, for example, Yang C, Mills D, Mathee K, Wang Y, Jayachandran K, Sikaroodi M, Gillevet P, Entry J, Narasimhan G (2006) An ecoinformatics tool for microbial community studies: Supervised classification of Amplicon Length Heterogeneity (ALH) profiles of 16S rRNA. Journal of Microbiological Methods 65(1):49-62.

In other embodiments, correlation network and correlation difference network methods can be used to associate microbiome signature with a particular phenotype with a statistical significant (P value) of less than 0.05. See, for example, Weckwerth W, Loureiro M E, Wenzel, Fiehn O (2004) Differential metabolic networks unravel the effects of silent plant phenotypes. PNAS 101(20):7809-7814.

Once an animal is identified as not having a particular positive phenotype, suitable intervention can be undertaken to alter the identity and/or the relative abundance of rumen microflora in the animal. Accordingly, the present invention also encompasses the identification of suitable therapeutic targets for intervention and the selection/development of suitable treatment protocols. Exemplary treatments include but are not limited to: eliminating or lessening microflora associated with the condition e.g. using antibiotics or other therapies, for example, therapies that are specific for eliminating or lessening the number of targeted microflora, without affecting or minimally affecting desirable microflora, if possible; or increasing microflora that compete with the unwanted microflora, and/or which are correlated with the positive phenotype, e.g. by administering probiotic and/or prebiotic supplements; by microfloral transplants (e.g. from animals having the positive phenotype, as described herein above).

Once an animal is identified as having a particular positive phenotype, it may be separated from the rest of the herd and classified as having the phenotype. According to one embodiment, the animal branded such that it is clear that it comprises this phenotype.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all to the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, to Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990);

Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND METHODS

Animal Handling and Sampling:

Healthy 2-year-old Israeli Holstein Friesian lactating cows were housed together (n=15) at the ARO dairy farm in Bet Dagan, Israel. The cows were selected for similar physical condition—age and weight—and were sampled during their first pregnancy, at the same stage of lactation. The cows were fed a diet consisting of 30% roughage and 70% concentrate ad libitum, provided once a day, which is the standard practice and feeding regimen in the facilities. Ruminal contents, collected via the cow's mouth using a stainless-steel stomach tube with a rumen vacuum sampler, were taken 1 hour after the morning feeding. Samples were immediately transferred to $CO_2$-containing centrifuge bottles to maintain anaerobic conditions, and kept on ice. Within 1 h of collection, the ruminal samples were processed in the laboratory.

Cow Physiological Parameters:

Physiological parameters were recorded using an in-house automated—computerized monitoring system designed to identify individual cows electronically and automatically record each cow's parameters. Milk yield (kg) of each cow was recorded for each milking and a daily average was calculated by automatic meters (Afimilk SAE, Afikim, Israel). Milk samples were collected in three sequential milkings on a weekly basis from the day cows were introduced to the high-concentrate diet until rumen sampling 5 weeks later. Analysis of fat, true protein, and lactose in the milk was performed by infrared analysis (Israeli Cattle Breeders Association laboratory, Caesaria, Israel) using a Milkoscan 4000 (Foss Electric, Hillerod, Denmark). Both residual feed intake (RFI) and feed-conversion ratio (FCR) were calculated according to the National Research Council. RFI evaluates energetic efficiency according to the difference between the animal's actual feed intake and its estimated feed intake over a specified period of time. Animals with low RFI values are considered to be more energetically efficient than those with high values. The independence of this method from growth and body size makes it suitable for comparisons between animals.

Bacterial extraction and DNA purification: Bacterial isolation was performed as follows. Briefly, samples were homogenized for 2 minutes in a blender, which was washed with 70% ethanol and distilled water between samples to avoid cross-contamination, and then centrifuged at 10,000 g. The supernatant was discarded and the pellet was dissolved 1:4 (g:ml) in extraction buffer (100 mM Tris-HCl, 10 mM ethylenediaminetetraacetic acid [EDTA], 0.15 M NaCl pH 8.0). The samples were then incubated at 4° C. for 1 hour to maximize the release of particle-associated bacteria from the ruminal contents. This was followed by 15 minutes centrifugation at 500 g to discard plant particles while the bacterial cells remained in suspension. The supernatant was then passed through four layers of new, sterile cheesecloth, and centrifuged (10,000 g, 25 minutes, 4° C.), and the pellets were kept at −20° C. until DNA extraction.

For DNA extraction, cells were lysed by bead disruption with phenol, and phenol/chloroform extraction of DNA was performed. DNA was then precipitated using isopropanol and the precipitate was resuspended in Tris-EDTA buffer and stored at −20° C. until analysis. Protocols for bacterial extraction and DNA purification were verified for reproducibility by performing duplicates for each sample and assessed by automated ribosomal spacer analysis (ARISA) for the whole bacterial community. Analysis of similarities (ANOSIM) was used in order to test whether there is a significant difference between the bacterial extraction and DNA purification methods coming from a given sample. This analysis revealed that there is no statistical difference between the replicates, indicating that the microbes and DNA extraction do not cause any differential bias across the samples. This can also be visualized by using cluster analysis dendrogram (FIG. 7).

454 Tag amplicon pyrosequencing and data analyses: 454 Amplicon pyrosequencing of the ruminal DNA samples was performed as described previously [Jami et al., 2012, PLoS One 7: e33306. doi: 10.1371]. The sequencing was done at the Research and Testing Laboratory (Lubbock, Tex.) using primers covering the 103- to 530-bp region of the 16S rRNA gene sequence which corresponds to the V2 and V3 regions (107 F: 5'-GGCGVACGGGTGAGTAA-3' (SEQ ID NO: 1) and 530 R: 5'-CCGCNGCNGCTGGCAC-3'; SEQ ID NO: 2). The tagging and sequencing protocol was as described by Dowd et al. [20]. Data quality control and analyses were mostly performed using the QIIME pipeline [21]. The UCLUST method [22] was selected for operational taxonomic unit (OTU) clustering with degree of similarity between sequences defined as ≥97% and ≥94% for OTU identity at the species and genus level, respectively. The present inventors used the representative sequence of each OTU to remove chimeric sequences using the ChimeraSlayer algorithm [23]. OTUs which clustered only one or two reads were manually removed. After constructing an OTU table, taxonomy was assigned using the BLAST algorithm with the Greengenes 16S rRNA reference database found at blogdotqiimedotorg designated "most recent Greengenes OTUs". All sequences used for this study were publicly deposited in the MG-RAST server, I.D no. 4483775.3.

Statistical analysis: Pearson correlation was used to correlate physiological parameters and bacterial composition using PAleontological STatistics (PAST) software [24] and plotted using the corrplot R package [25].

Results

The aim of this study was to determine whether there are any correlations between the bacterial community residing in the cow rumen and the physiology of the individual cow hosts. The present inventors analyzed 15 lactating dairy cows, whose ruminal bacterial communities had been previously pyrosequenced [12], under a high-energy diet. Their rumen fluid was sampled during lactation and their physiological parameters were recorded and calculated. These included milk yield, milk content (carbohydrate, protein, and fat), pH, dry matter intake (DMI) and RFI, which serves to evaluate the animal's feed efficiency. After quality-filtering based on length (<200 bp) and quality of the reads, 141,344 reads were obtained averaging 338 bp each (Table 1, herein below).

TABLE 1

| Cow # | Mean read length | Number of reads per animal |
|---|---|---|
| 2918 | 332 ± 72 | 9940 |
| 2669 | 348 ± 83 | 9690 |
| 2858 | 342 ± 81 | 9125 |
| 2961 | 334 ± 85 | 11532 |
| 2871 | 342 ± 72 | 7868 |
| 2712 | 339 ± 82 | 9536 |
| 2938 | 335 ± 81 | 10165 |
| 2833 | 342 ± 74 | 6858 |
| 2619 | 339 ± 81 | 8367 |
| 2860 | 336 ± 83 | 10241 |
| 2876 | 338 ± 77 | 8135 |
| 2810 | 341 ± 73 | 7322 |
| 2923 | 331 ± 71 | 8803 |
| 2927 | 336 ± 81 | 8537 |
| 2926 | 334 ± 86 | 15225 |
| Average | 338 ± 80 | 9422 ± 2020 |

The length and number of the reads per animal sampled after quality filtering, chimeric sequences and singletons-doubletons removal is presented in Table 2, herein below.

TABLE 2

| Cow # | Mean read length | Number of reads per animal |
|---|---|---|
| 2918 | 332 ± 72 | 9940 |
| 2669 | 348 ± 83 | 9690 |
| 2858 | 342 ± 81 | 9125 |
| 2961 | 334 ± 85 | 11532 |
| 2871 | 342 ± 72 | 7868 |
| 2712 | 339 ± 82 | 9536 |
| 2938 | 335 ± 81 | 10165 |
| 2833 | 342 ± 74 | 6858 |
| 2619 | 339 ± 81 | 8367 |
| 2860 | 336 ± 83 | 10241 |
| 2876 | 338 ± 77 | 8135 |
| 2810 | 341 ± 73 | 7322 |
| 2923 | 331 ± 71 | 8803 |
| 2927 | 336 ± 81 | 8537 |
| 2926 | 334 ± 86 | 15225 |
| Average | 338 ± 80 | 9422 ± 2020 |

Overall, 17 phyla were detected, but only 7 were found in all cows (FIG. 1A). The three dominant phyla observed, in agreement with all studies of mammalian gut microbiota, were Bacteroidetes, Firmicutes and Proteobacteria, as previously described and reported in other mammalian gut studies [2], [12], [26]. However, there was a large variation in the abundance of the two main phyla—Bacteroidetes and Firmicutes—between the different animals [13]. Although Bacteroidetes was more abundant in most of the samples, some exhibited a higher percentage of Firmicutes compensating for a lower abundance of Bacteroidetes (FIG. 1B). The Firmicutes-to-Bacteroidetes ratio was found to be strongly correlated with daily milk-fat yield (Pearson R=0.72, P=$2\times10^{-3}$) (FIG. 2). This finding mirrors that in mice, where a decreased amount of Bacteroidetes in the microbiota was correlated with increased fat in the blood and tissue [4].

The present inventors then compared the physiological parameters with the microbiota at the genus level. To confirm adequate sequencing depth for these analyses, to they generated rarefaction curves for each sample as a function of the number of observed OTUs (OTU≥94%, defined as genus level) and found their coverage to be sufficient for further analyses at the genus level (FIG. 5). Overall, 151 genera were detected in the samples. The present inventors focused their analysis on the more abundant taxa, and only genera that were in at least half of the samples at over 0.1% of the microbiota in at least one animal were included in the analysis. Therefore, only 42 genera were compared to the physiological parameters. These included those found to be part of the core community in a previous study, i.e., shared by all of the animals sampled, and accounting for over 90% of the overall rumen bacterial OTUs [12]. The present assumption was that these 42 genera represent important components of the healthy rumen ecosystem, and would therefore be more likely to reveal a connection between host physiology and the bacterial community residing in its rumen. A correlation matrix was created to evaluate each of these genera with each physiological parameter (FIG. 3). *Prevotella*, the most abundant genus in the samples (up to 72% in some samples), showed a significantly negative correlation (Pearson R=−0.69, P=$5\times10^{-3}$) with milk-fat yield, explaining most of the Bacteriodetes' negative correlation to this parameter, as well as its correlation with Firmicutes-to-Bacteroidetes ratio. Firmicutes, on the other hand, was composed of many lower-abundance genera, only a fraction of which compensated for the decreasing abundance of *Prevotella* in the samples. Analysis of the genera from the phylum Firmicutes revealed that 9 out of the 23 genera analyzed (FIGS. 4 and 6) were more abundant in samples with low levels of *Prevotella*, and 5 of these were correlated with milk-fat yield; most of these belonged to the order Clostridiales—the genus *Eubacterium* (Pearson R=0.62, P=0.012) and the family Lachnospiraceae (Pearson R=0.62, P=0.014) (FIG. 3), and some belonged to the class Negativicutes, only recently defined as such, and formerly members of the Clostridia, such as the genus *Dialister* (Pearson R=0.64, P=0.009). Some of the genera belonging to Firmicutes were of relatively similar abundance between the samples regardless of the abundance of *Prevotella*, whereas others were found in higher abundance in samples with a low abundance of *Prevotella*. Two genera, *Dialister* and *Lactobacillus*, were almost nonexistent in samples with over 50% *Prevotella*, whereas they were present in all samples with less than 50% *Prevotella* (FIGS. 4 and 6). Genera belonging to other phyla also showed a correlation with milk-fat yield, such as the genus *Desulfovibrio*, belonging to the Proteobacteria. From the phylum Actinobacteria, both *Bifidobacterium* and *Lactobacillus*, widely used as probiotics, also showed a positive correlation to milk-fat yield, along with the genus *Bulleidia*, belonging to the Firmicutes. Whereas the correlations between the microbiota and milk-fat yield were found to be the strongest, the present inventors also detected both negative and positive correlations with other parameters related to the host's physiology and milk composition, including milk lactose and protein contents. With respect to host physiology, some bacteria were correlated with the variation in ruminal pH between cows, such as the genus *Rosburia* (Pearson R=−0.5, P=0.06). One study reported that members of this taxon are affected by changes in pH 1281, with optimal growth under slightly acidic conditions. Those authors suggested that this genus is affected by either pH or competitors that emerge at more neutral pH values. Interestingly, significant positive correlations were observed between four genera, all belonging to the order Coriobacteriales, and milk-lactose content. These were Atopobium and Adlercreutzia, and two unknown genera belonging to the order Coriobacteriales, one of them also positively correlating with average milk yield (Pearson R=0.57 P=0.027) (FIG. 3). The fact that these taxa are phylogenetically related suggests that they share functions that affect the host's physiology in a similar manner. In addition, both *Mitsuokella* and *Desulfovibrio* were positively correlated with milk-lactose yield (Pearson R=0.59 for both genera). No significant correlation was detected between the bacterial community and RFI; however, a positive, albeit nonsignificant correlation (Pearson R=0.51, P=0.055) was detected between an unclassified genus from the putative order RF39, found in all of the animals sampled, and RFI. This genus, although little studied, is found in many gut environments [12], [29], including the rumen, hinting at a potentially crucial role in the gut of many species. Nevertheless, additional sampling is required to determine whether this taxon is associated with feed efficiency in cattle.

Overall, the present findings in this study show remarkable similarities with those in other mammalian host systems regarding their interaction with the gut microbiome. This suggests an underlying mechanism of acquisition and energy utilization that may be common to many of the studied gut systems, regardless of the apparent phylogenetic distances between the hosts.

The current study suggests a connection between the physiological parameters to of dairy cattle and their resident rumen bacteria and reveals potential candidate taxa that may prove useful for future inoculation studies.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Turnbaugh P J, Gordon J I (2009) The core gut microbiome, energy balance and obesity. J Physiol 587: 4153-4158. doi: 10.1113/jphysiol.2009.174136
Arumugam M, Raes J, Pelletier E, Le Pastier D, Yamada T, et al. (2011) Enterotypes of the human gut microbiome. Nature 473: 174-180. doi: 10.1038/nature09944
Ley R E, Turnbaugh P J, Klein S, Gordon J I (2006) Microbial ecology: human gut microbes associated with obesity. Nature 444: 1022-1023. doi: 10.1038/4441022a
Turnbaugh P J, Ley R E, Mahowald M A, Magrini V, Mardis E R, et al. (2006) An obesity-associated gut microbiome with increased capacity for energy harvest. Nature 444: 1027-1031. doi: 10.1038/nature05414
Ridaura V K, Faith J J, Rey F E, Cheng J, Duncan A E, et al. (2013) Gut microbiota from twins discordant for obesity modulate metabolism in mice. Science 341: 1241214. doi: 10.1126/science.1241214
Flint H J, Bayer E A, Rincon M T, Lamed R, White B A (2008) Polysaccharide utilization by gut bacteria: potential for new insights from genomic analysis. Nat Rev Microbiol 6: 121-131. doi: 10.1038/nrmicro1817
Mizrahi I (2011) The Role of the Rumen Microbiota in Determining the Feed Efficiency of Dairy Cows. In: Rosenberg E, Gophna U, editors. Beneficial Microorganisms in Multicellular Life Forms: Springer Berlin Heidelberg.
Mizrahi I (2013) Rumen Symbioses. In: Eugene Rosenberg, Edward F DeLong, Stephen Lory, Erko Stackebrandt, Thompson F, editors. The Prokaryotes: Springer Berlin Heidelberg. pp. 533-544.
Brute J M, Antonopoulos D A, Miller M E, Wilson M K, Yannarell A C, et al. (2009) Gene-centric metagenomics of the fiber-adherent bovine rumen microbiome reveals forage specific glycoside hydrolases. Proc Natl Acad Sci USA 106: 1948-1953. doi: 10.1073/pnas.0806191105
Hurtaud C, Rulquin H, Verite R (1993) Effect of infused volatile fatty acids and caseinate on milk composition and coagulation in dairy cows. J Dairy Sci 76: 3011-3020. doi: 10.1051/animres:19920156
Hemandez-Sanabria E, Guan L L, Goonewardene L A, Li M, Mujibi D F, et al. (2010) Correlation of particular bacterial PCR-denaturing gradient gel electrophoresis patterns with bovine ruminal fermentation parameters and feed efficiency traits. Appl Environ Microbiol 76: 6338-6350. doi: 10.1128/aem.01052-10
Jami E, Mizrahi I (2012) Composition and Similarity of Bovine Rumen Microbiota across Individual Animals. PLoS One 7: e33306. doi: 10.1371/journal.pone.0033306
Li M, Penner G B, Hemandez-Sanabria E, Oba M, Guan L L (2009) Effects of sampling location and time, and host animal on assessment of bacterial diversity and fermentation parameters in the bovine rumen. J Appl Microbiol 107: 1924-1934. doi: 10.1111/j.1365-2672.2009.04376.x
Jami E, Shabtay A, Nikbachat M, Yosef E, Miron J, et al. (2012) Effects of adding a concentrated pomegranate-residue extract to the ration of lactating cows on in vivo digestibility and profile of rumen bacterial population. J Dairy Sci 95: 5996-6005.
National Research., Council N.R.C. (2001) Nutrient Requirements of Dairy Cattle. 7th rev. ed. Natl. Acad. Sci., Washington, D C.
Archer J A, Richardson E C, R M H, P F A (1999) Potential for selection to improve efficiency of feed use in beef cattle. Aust J Agric Res 50: 147-162. doi: 10.1071/a98075
Koch R M, Swiger L A, Chambers D, Gregory K E (1963) Efficiency of feed use in beef cattle. J Anim Sci 22: 486-494.
Stevenson D M, Weimer P J (2007) Dominance of Prevotella and low abundance of classical ruminal bacterial species in the bovine rumen revealed by relative quantification real-time PCR. Appl Microbiol Biotechnol 75: 165-174. doi: 10.1007/s0025 3-006-0802-y
Dehority B A, Grubb J A (1980) Effect of short-term chilling of rumen contents on viable bacterial numbers. Appl Environ Microbiol 39: 376-381.
Dowd S E, Callaway T R, Wolcott R D, Sun Y, McKeehan T, et al. (2008) Evaluation of the bacterial diversity in the feces of cattle using 16S rDNA bacterial tag-encoded FLX amplicon pyrosequencing (bTEFAP). BMC Microbiol 8: 125. doi: 10.1186/1471-2180-8-125
Caporaso J G, Kuczynski J, Stombaugh J, Bittinger K, Bushman E D, et al. (2011) QIIME allows analysis of high-throughput community sequencing data. Nat Methods 7: 335-336. doi: 10.1038/nmeth.f.303
Edgar R C (2010) Search and clustering orders of magnitude faster than BLAST. Bioinformatics 26: 2460-2461. doi: 10.1093/bioinformatics/btq461
Haas B J, Gevers D, Earl A M, Feldgarden M, Ward D V, et al. (2011) Chimeric 16S rRNA sequence formation and detection in Sanger and 454-pyrosequenced PCR amplicons. Genome Res 21: 494-504. doi: 10.1101/gr.112730.110

Hammer Ø, Harper D A T, Ryan P D (2001) PAST: Paleontological Statistics Software Package for Education and Data Analysis. Palaeontologia Electronica 4: 9 pp.

Wei T (2012) Package 'corrplot'—Visualization of a correlation matrix v0.60. cran.r-project.org. Available:

Ochman H, Worobey M, Kuo C H, Ndjango J B, Peeters M, et al. (2010) Evolutionary relationships of wild hominids recapitulated by gut microbial communities. PLoS Biol 8: e1000546. doi: 10.1371/journal.pbio.1000546

Chiquette J, Allison M J, Rasmussen M A (2008) *Prevotella bryantii* 25A used as a probiotic in early-lactation dairy cows: effect on ruminal fermentation characteristics, milk production, and milk composition. J Dairy Sci 91: 3536-3543.

Walker A W, Duncan S H, McWilliam Leitch E C, Child M W, Flint H J (2005) pH and peptide supply can radically alter bacterial populations and short-chain fatty acid ratios within microbial communities from the human colon. Appl Environ Microbiol 71: 3692-3700. doi: 10.1128/aem.71.7.3692-3700.2005

Lin A, Bik E M, Costello E K, Dethlefsen L, Hague R, et al. (2013) Distinct distal gut microbiome diversity and composition in healthy children from Bangladesh and the United States. PLoS One 8: e53838. doi: 10.1371/journal.pone.0053838

Jami E, Israel A, Kotser A, Mizrahi I (2013) Exploring the bovine rumen bacterial community from birth to adulthood. ISME J 7: 1069-1079. doi: 10.1038/ismej.2013.2

What is claimed is:

1. A method of mimicking a phenotype of a first ruminating animal in a second ruminating animal, wherein said phenotype is selected from the group consisting of milk production, meat quality, milk quality and milk quantity, comprising administering to the second ruminating animal a microbial composition of the rumen of the first ruminating animal, wherein the relative abundance of microbial species in said composition is identical to the relative abundance of said microbal species of the rumen of the first ruminating animal, wherein said first and said second ruminating animal are of an identical species, thereby mimicking the phenotype of the first ruminating animal in the second ruminating animal, wherein said second ruminating animal is a newborn.

2. The method of claim 1, wherein said administering is performed more than one time.

3. The method of claim 1, wherein said microbial composition is comprised in a composition selected from the group consisting of a feed, a silage and an enema.

4. The method of claim 1, wherein said second ruminating animal is treated with an antibiotic composition prior to the administering.

5. The method of claim 1, wherein said phenotype is milk quantity and milk quality.

6. A method of mimicking a phenotype of a first ruminating animal in a second ruminating animal, wherein said phenotype is selected from the group consisting of milk production, meat quality, milk quality and milk quantity, comprising administering to the second ruminating animal a microbial composition of the rumen of the first ruminating

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (5)..(5)
<223> OTHER INFORMATION: V is A, C or G

<400> SEQUENCE: 1
ggcgvacggg tgagtaa                                              17

<210> SEQ ID NO 2
<211> LENGTH: 16
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 2
ccgcngcngc tggcac                                               16
``` animal, wherein the relative abundance of microbial species in said composition is identical to the relative abundance of said microbal species of the rumen of the first ruminating animal, wherein said first and said second ruminating animal are of an identical species, thereby mimicking the phenotype of the first ruminating animal in the second ruminating animal, wherein said second ruminating animal is treated with an antibiotic composition prior to the administering.

7. The method of claim 6, wherein said administering is performed more than one time.

8. The method of claim 6, wherein said microbial composition is comprised in a composition selected from the group consisting of a feed, a silage and an enema.

9. The method of claim 6, wherein said second ruminating animal is not older than one month.

10. The method of claim 6, wherein said second ruminating animal is a newborn.

11. The method of claim 6, wherein said phenotype is milk quantity and milk quality.

\* \* \* \* \*